United States Patent [19]

Kurono et al.

[11] 4,275,075
[45] Jun. 23, 1981

[54] 15-CYLOBUTYL-TRANS-$\Delta^2$-PROSTAGLANDIN ANALOGUES

[75] Inventors: Masayasu Kurono, Osaka; Hisao Nakai, Takatau-ku; Shigeru Sakuyama, Nagaokakyo, all of Japan

[73] Assignee: ONO Pharmaceutical Co. Ltd., Osaka, Japan

[21] Appl. No.: 915,493

[22] Filed: Jun. 14, 1978

[30] Foreign Application Priority Data

Jun. 14, 1977 [GB] United Kingdom ............... 24867/77

[51] Int. Cl.$^3$ ......................................... C07C 177/00
[52] U.S. Cl. .................................. 424/305; 536/103; 542/426; 560/118; 560/231; 562/500; 568/816; 424/317; 568/367
[58] Field of Search ....................... 560/118; 562/500; 424/305, 317

[56] References Cited

U.S. PATENT DOCUMENTS 4,087,620   5/1978   Hayashi et al. ...................... 560/121

*Primary Examiner*—Robert Gerstl
*Attorney, Agent, or Firm*—Stephen I. Miller; Stephen Raines; Albert H. Graddis

[57] ABSTRACT

The present invention relates to prostaglandin analogues of the general formula:

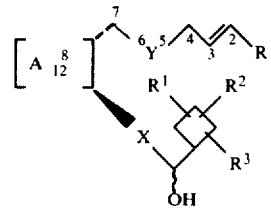

[wherein A represents a grouping of the formula:

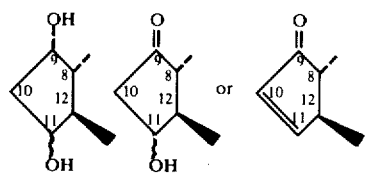

X represents trans-vinylene or ethylene and Y represents cis-vinylene or ethylene, R represents a group of the formula —COOR$^4$, in which R$^4$ represents hydrogen or straight- or branched-chain alkyl of 1 to 12 carbon atoms, or a group of the formula —CH$_2$OR$^5$, in which R$^5$ represents hydrogen or alkylcarbonyl of 2 to 5 carbon atoms and R$^1$, R$^2$ and R$^3$, which may be the same or different, each represent hydrogen, straight- or branched-chain alkyl of 1 to 12 carbon atoms, or an aryl group unsubstituted or substituted by one, two or three substituents selected from alkyl, alkoxy, alkylthio, monoalkylamino and dialkylamino groups and halogen atoms, the alkyl groups or moieties of the said groups containing from 1 to 5 carbon atoms in a straight- or branched-chain, with the proviso that at least one of the symbols R$^1$, R$^2$ and R$^3$ is other than hydrogen and the double bond between C$_2$–C$_3$ is trans] and cyclodextrin clathrates of such prostaglandin analogues and, when R$^4$ in the group - COOR$^4$ represents hydrogen, nontoxic salts thereof, which exhibit characteristic prostaglandin-like activities.

9 Claims, No Drawings

15-CYLOBUTYL-TRANS-Δ²-PROSTAGLANDIN ANALOGUES

This invention is concerned with new prostaglandin analogues.

Prostaglandins are derivatives of prostanoic acid which has the following formula:

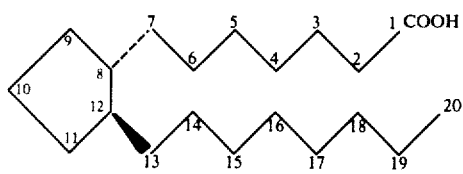

Various types of prostaglandins are known, the types depending inter alia on the structure and substituents on the alicyclic ring. For example, the alicyclic rings of prostaglandins F(PGF), E(PGE), and A(PGA) have the structures:

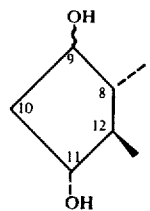 , 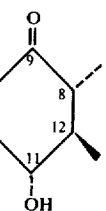 and 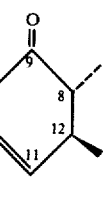

(II)                  (III)                (IV)

respectively. The dotted lines in the foregoing formulae and in other formulae throughout this specification denote, in accordance with generally accepted rules of nomenclature, that the attached grouping lies behind the general plane of the ring system, i.e. that the grouping is in α-configuration, the thickened lines ⟍ denote that the grouping lies in front of the general plane of the system, i.e. that the grouping is in β-configuration, and the wavy line indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$-$C_{14}$(trans-$\Delta^{13}$) and $PG_2$ compounds have a cis-double bond between $C_5$-$C_6$ and a trans-double bond between ($C_{13}$-$C_{14}$(cis-$\Delta^5$, trans-$\Delta^{13}$). For example, prostaglandin $F_{1\alpha}$ ($PGF_{1\alpha}$) and prostaglandin $E_1$ ($PGE_1$) are characterized by the following structures V and VI.

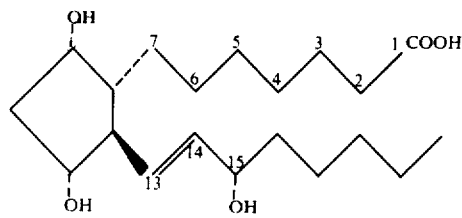

and

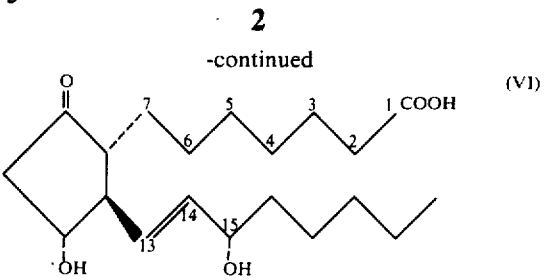

respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are eliminated from the aliphatic group attached to the 12-position of the alicyclic ring of the prostaglandins the compounds are known, in accordance with the usual rules of organic nomenclature, or nor-prostaglandins and, when more than one methylene group is eliminated, the number is indicated by di-, tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs and PGAs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and an purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs and PGAs have vasodilator and diuretic activities. PGEs are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree. It has now been found that by replacing the n-butyl group at the end of the aliphatic group linked to the 12-position of the alicyclic ring of prostaglandins F, E and A by an alkyl or aryl-substituted cyclobutyl group, introducing a trans-double bond between the carbon atoms in the 2- and 3-positions of such prostaglandins and optionally replacing the carboxy group (—COOH) on the aliphatic group attached to the 8-position of such prostaglandins by a hydroxymethyl (—CH$_2$OH) or acylated hydroxymethyl group, new prostaglandin analogues are obtained which possess the pharmacological properties of the 'natural' prostaglandins and are, in some aspects of their activities, an improvement, for example they possess an enhanced strength of activity or a prolonged duration of activity.

The present invention accordingly provides the new prostaglandin analogues of the general formula:

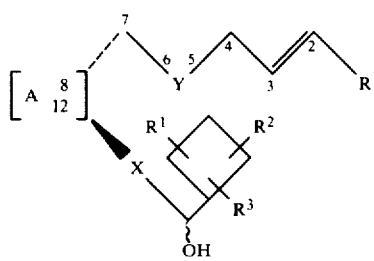

(VII)

[wherein A represents a grouping of formula IV as indicated hereinbefore or a grouping of the formula:

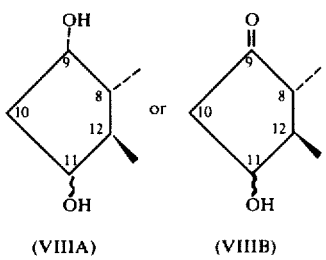

(VIIIA)        (VIIIB)

X represents trans-vinylene (i.e. —CH=CH—), or ethylene (i.e. —CH$_2$—CH$_2$—) and Y represents cis-vinylene or ethylene, R represents a group of the formula —COOR$^4$, in which R$^4$ represents a hydrogen atom or a straight- or branched-chain alkyl group containing from 1 to 12 carbon atoms, or a group of the formula —CH$_2$OR$^5$, in which R$^5$ represents a hydrogen atom or an alkylcarbonyl group containing from 2 to 5 carbon atoms and R$^1$, R$^2$ and R$^3$, which may be the same or different, each represent a hydrogen atom, a straight- or branched-chain alkyl group containing from 1 to 12 carbon atoms, or an aryl group unsubstituted or substituted by one, two or three substituents selected from alkyl, alkoxy, alkylthio, monoalkylamino and dialkylamino groups and halogen atoms, the alkyl groups or moieties of the said groups containing from 1 to 5 carbon atoms in a straight or branched-chain, with the proviso that at least one of the symbols R$^1$, R$^2$ and R$^3$ is other than hydrogen] and cyclodextrin clathrates of such prostaglandin analogues and, when R$^4$ in the group —COOR$^4$ represents a hydrogen atom, non toxic (e.g. sodium) salts thereof. It is to be understood that in general formula VII and formulae subsequently appearing in this specification the double bond in position C$_2$-C$_3$ is trans. Preferably the hydroxy groups depicted in formulae VII, VIIIA and VIIIB in α-configuration or β-configuration are attached to the carbon atom in α-configuration.

The present invention is concerned with all compounds of general formula VII in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VII have at least three centres of chirality, at the alicyclic ring carbon atoms of group A identified as 8 and 12 and at the C-15 carbon atom which has attached to it a hydroxy group. Still further centres of chirality occur when the alicyclic group A carries hydroxy groups on the carbon atoms in positions 9 and 11 (i.e. when the ring is that of formula VIIIA) or a hydroxy group in position 11 (i.e. when the ring is that of formula VIIIB). In addition, centres of chirality may occur at the carbon atoms of substituted cyclobutane rings in prostaglandin analogues of formula VII and further centres of chirality may occur when at least one of the symbols R$^1$, R$^2$, and R$^3$ represents a branched-chain alkyl group.

The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration are to be considered within the scope of general formula VII.

According to a feature of the present invention, the prostaglandin analogues of general formula VII, wherein R represents a group —COOR$^4$, in which R$^4$ is as hereinbefore defined, and the other symbols are as hereinbefore defined, i.e. compounds of the general formula:

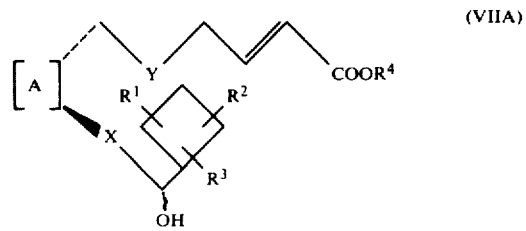

(VIIA)

(wherein the various symbols are as hereinbefore defined) are prepared by the process which comprises hydrolyzing a cyclopentane derivative of the general formula:

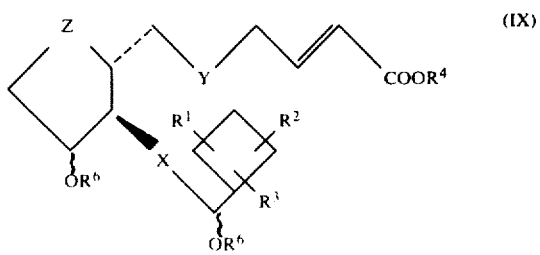

(IX)

(wherein Z represents

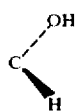

or C=O, $R^6$ represents a 2-tetrahydrofuranyl group, a 1-ethoxyethyl group or a 2-tetrahydropyranyl group unsubstituted or substituted by at least one alkyl group, and the other symbols are as hereinbefore defined) to convert to hydroxy groups the groups $OR^6$ to obtain a PGF or PGE compound of the general formula:

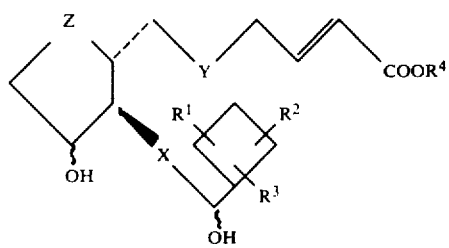

(VIIB)

(wherein the various symbols are as hereinbefore defined), and if desired, converting by methods known per se the PGE alicyclic ring of a compound of general formula VIIB (Z represents C=O) to that of a PGA compound. By the term methods known per se as used in this specification is meant methods heretofore used or described in the chemical literature.

The groups $OR^6$ of the compounds of general formula IX (preferably such groups are 2-tetrahydropyranyloxy) may be converted to hydroxy group by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60° C. (preferably at a temperature below 45° C.) with an acid mixture, e.g. a mixture of hydrochloric acid with tetrahydrofuran or methanol, or a mixture of acetic acid, water and tetrahydrofuran. The products of formula VIIB may be purified by column chromatography on silica gel, which procedure may, when the starting material of formula IX is a mixture of compounds with the $OR^6$ group in the 15-position in α- and β-configurations, lead to a separation of the resulting 15α-hydroxy and 15β-hydroxy isomers of formula VIIB.

The PGE compounds of general formula VIIB (Z represents C=O) can be converted into the corresponding PGA compounds of general formula VII (A represents a grouping of formula IV) by subjecting the PGEs to dehydration using an aqueous solution of an organic or inorganic acid having a higher concentration than that employed for hydrolysing the groups $OR^6$ of compounds of general formula IX, e.g. 1 N hydrochloric acid or acetic acid and heating at a temperature of 30°-60° C. If desired, simultaneous hydrolysis and dehydration under acidic conditions as hereinbefore described may be effected on compounds of general formula IX, wherein Z represents C=O and the other symbols are as hereinbefore defined, to produce directly PGA compounds of formula VII (A represents a grouping of formula IV).

Compounds of general formula VIIB, wherein $R^4$ represents an alkyl group containing from 1 to 12 carbon atoms and Z represents C=O, may, if desired, be converted to corresponding acids of general formula VIIB, i.e. wherein $R^4$ represents a hydrogen atom, by treatment with baker's yeast, cf. C. J. Sih et al, J. Amer. Chem. Soc., 94, 3643 (1972).

Compounds of general formula IX, wherein Z represents

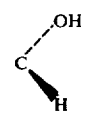

and the other symbols are as hereinbefore defined i.e. compounds of the general formula:

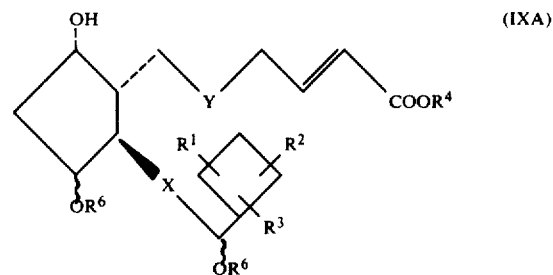

(IXA)

(wherein the various symbols are as hereinbefore defined) may be prepared by the process which comprises reacting a compound of the general formula:

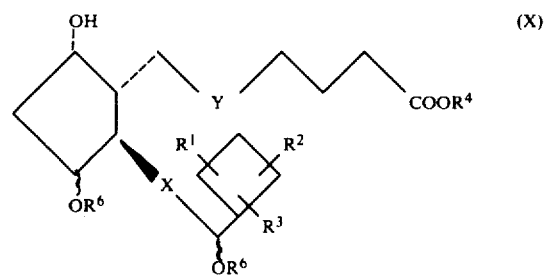

(X)

(wherein the various symbols are as hereinbefore defined) with a compound of the general formula:

(XI)

(wherein $R^7$ and $R^8$ each represents an alkyl group containing from 1 to 6 carbon atoms or a cycloalkyl group containing from 3 to 6 carbon atoms) to obtain a lithium esterenolate of the general formula:

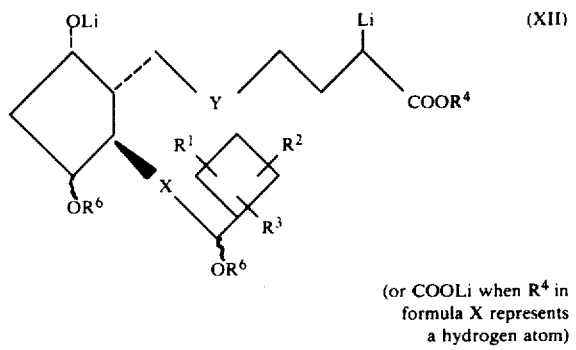

(or COOLi when $R^4$ in formula X represents a hydrogen atom)

(wherein the various symbols are as hereinbefore defined), reacting the lithium esterenolate with benzeneselenenyl bromide (i.e. $\phi$SeBr in which $\phi$ represents the phenyl radical) or diphenyldiselenide or a dialkyl- or diphenyl-disulphide of the formula $R^9SSR^9$, wherein the symbols $R^9$ both represent alkyl groups containing from 1 to 4 carbon atoms or phenyl radicals, hydrolysing the resulting intermediate to obtain a compound of the general formula:-

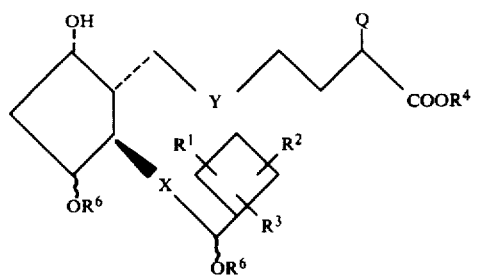

(wherein Q represents —Se$\phi$, in which $\phi$ is as hereinbefore defined, or a group —$SR^9$, in which $R^9$ is as hereinbefore defined, and the other symbols are as hereinbefore defined), treating the resulting compound with hydrogen peroxide or sodium periodate, and decomposing the resulting compound of the general formula:

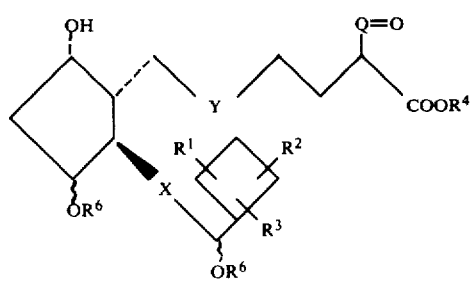

(wherein the various symbols are as hereinbefore defined) to convert the grouping

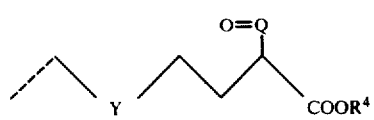

attached to the 8-position of the cyclopentane ring to a trans-$\Delta^2$-grouping

wherein $R^4$ is as hereinbefore defined.

The reaction between the prostaglandin compound of general formula X and the lithiated amine of general formula XI is carried out in an organic solvent medium, for example, when $R^4$ represents an alkyl group, by adding dropwise a solution of a prostaglandin ester of formula X in tetrahydrofuran to a solution of an amine of formula XI in tetrahydrofuran at a low temperature, e.g. $-78°$ C., or, when $R^4$ in general formula X represents a hydrogen atom, in tetrahydrofuran in the presence of hexamethylphosphoramide at 0° C., the ratio of the molecular equivalents of the compounds of formula X to XI in the reaction mixture being suitably adjusted to obtain a lithium esterenolate of formula XII. In the case where a prostaglandin ester is employed as reactant, after completion of the addition of the prostaglandin solution to the amine solution, the reaction mixture is stirred at the same temperature for about 30 minutes to obtain a solution of lithium esterenolate of formula XII. In the case where a prostaglandin acid is employed as reactant ($R^4$ represents a hydrogen atom), the reaction mixture is stirred at room temperature for about 30 minutes to obtain a solution of the lithium esterenolate of formula XII.

The reaction between the lithium esterenolate of formula XII and benzeneselenenyl bromide, diphenyldiselenide or a dialkyl- or diphenyl-disulphide, is preferably carried out in tetrahydrofuran, hexamethylphosphoramide, diethyl ether, n-pentane or n-hexane or a mixture of two or more of them, tetrahydrofuran being the preferred solvent medium, at a low temperature when $R^4$ in formula XII represents an alkyl group, e.g. $-78°$ C., or, when $R^4$ in formula XII represents a hydrogen atom, at 0° C. Thus, to the lithium esterenolate solution obtained as described above there is added a solution in tetrahydrofuran of benzeneselenenyl bromide, diphenyldiselenide or a dialkyl- or diphenyl-disulphide, the temperature of the two solutions being $-78°$ C. or 0° C. according to whether an ester or acid of formula XII, respectively, is the reactant. The reaction mixture is then stirred (when $R^4$ in formula XII is an alkyl group) at $-78°$ C. (a) for one hour when a selenium compound is the reactant or (b) for 30 minutes when a disulphide is the reactant, and subsequently at ambient temperature, e.g. 15° C. for 30 minutes, or (when $R^4$ in formula XII is a hydrogen atom) at room temperature for 1 hour 30 minutes. After addition of, for example, a small amount of a saturated aqueous ammonium chloride solution to the solution of the resulting prostaglandin intermediate to hydrolyze it, the prouct of formula XIII is extracted with ethyl acetate.

If desired, the intermediate esters of general formula XIII wherein $R^4$ represents an alkyl group may be converted to the corresponding acids of general formula XIII, i.e. wherein $R^4$ represents a hydrogen atom, by hydrolysis under alkaline conditions. The hydrolysis of the esters under alkaline conditions may be effected with an aqueous solution of an alkali metal, e.g. sodium or potassium, hydroxide or carbonate in the presence of a water-miscible organic solvent, e.g. tetrahydrofuran or an alkanol containing from 1 to 4 carbon atoms, e.g. methanol.

When the product of formula XIII is a compound wherein Q represents —SEφ, φ being as hereinbefore defined, the product is then treated with 5 to 7 molecular equivalents of hydrogen peroxide in a mixture of ethyl acetate and tetrahydrofuran or methanol at a temperature of 30° C. or below, or with 5 molecular equivalents of sodium periodate in the presence of a lower alkanol, preferably methanol, and water, at a temperature below 20° C., preferably for about 24 hours, to form a compound of formula XIV wherein O=Q— represents —Se(O), and stirring of the reaction mixture at a temperature of 25° to 30° C. for one hour results in decomposition of the compound to a trans-$\Delta^2$-prostaglandin analogue of general formula IXA, which can be separated from the reaction medium by methods known per se and, if desired, purified by column chromatography on silica gel.

When the product of formula XIII is a compound wherein Q is a group —$SR^9$, $R^9$ being as hereinbefore defined, the product is treated with hydrogen peroxide or sodium periodate in the same way as hereinbefore described for a product of formula XIII wherein Q is phenylseleno to obtain a compound of general formula XIV wherein Q is a group —$SR^9$, $R^9$ being as hereinbefore defined, which can be separated from the reaction medium by methods known per se.

When the compound of formula XIV is one wherein Q represents an alkylthio group —$SR^9$, wherein $R^9$ represents an alkyl group containing from 1 to 4 carbon atoms, the compound is dissolved in toluene and the solution stirred, preferably in the presence of a small amount of calcium carbonate, at a temperature of 100° to 120° C. for a period ranging from 5 to 24 hours to decompose the compound to a trans-$\Delta^2$-prostaglandin analogue of general formula IXA. When the compound of general formula XIV is one wherein Q represents the phenylthio group, the compound is dissolved in carbon tetrachloride and the solution stirred, preferably in the presence of a small amount of calcium carbonate, at a temperature of about 50° C. for a period ranging from 5 to 24 hours to decompose the compound to a trans-$\Delta^2$-prostaglandin analogue of general formula IXA.

Compounds of general formula IX, wherein Z represents C=O, and the other symbols are as hereinbefore defined, may be obtained from compounds of general formula IX, wherein Z represents

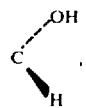

and the other symbols are as hereinbefore defined by methods known per se for the conversion of a hydroxy group in the 9-position of a prostaglandin compound to an oxo group, for example by means of a chromic acid solution (e.g. obtained from chromium trioxide, manganese sulphate, sulphuric acid and water) or Jones' reagent.

The method hereinbefore described for the preparation of prostaglandin analogues of general formula VII may be represented by the series of reactions depicted schematically below in Scheme A, wherein the various symbols are as hereinbefore defined.

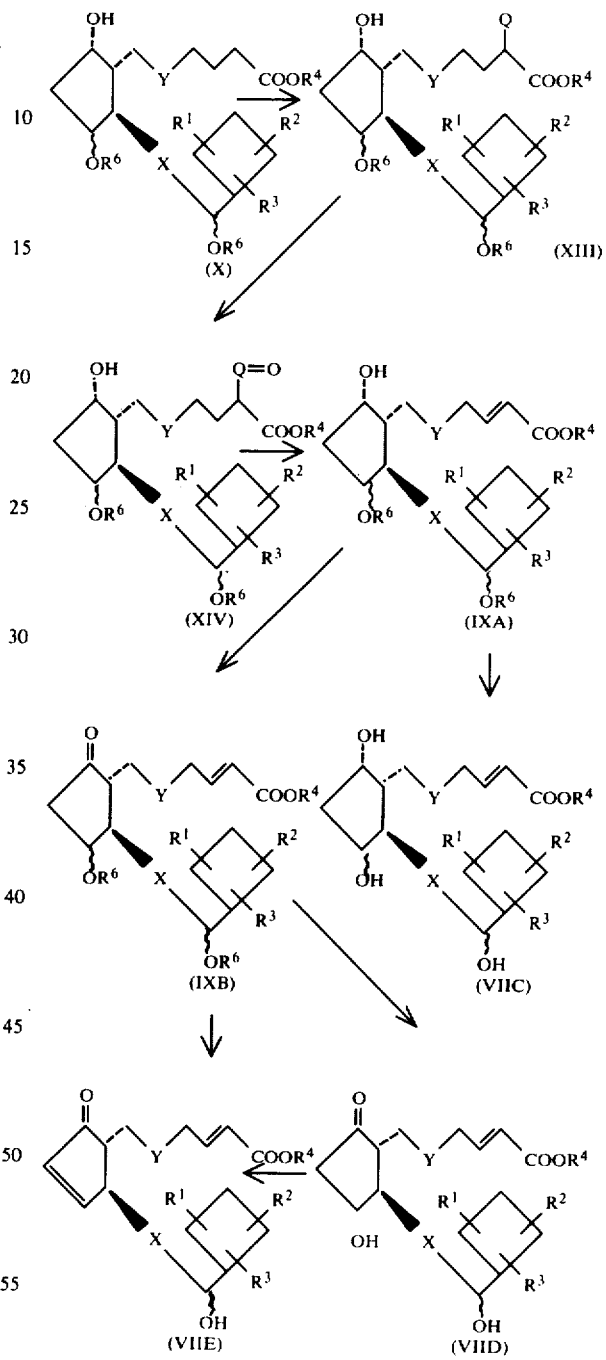

The starting materials of general formula X, wherein $R^4$ represents a straight- or branched-chain alkyl group containing from 1 to 12 carbon atoms and the other symbols are as hereinbefore defined, may be prepared from the corresponding acids of the general formula:

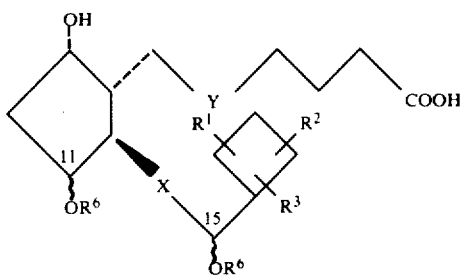

(wherein the various symbols are as hereinbefore defined) by esterification, for example by reaction with (i) the appropriate diazoalkane compound, e.g. diazomethane in an inert solvent, e.g. diethyl ether, at a temperature of from −10° to 25° C., and preferably 0° C., (ii) the appropriate alcohol in the presence of dicyclohexylcarbodiimide as condensing agent, or (iii) the appropriate alcohol following the formation of a mixed acid anhydride by adding a tertiary amine and then a pivaloyl halide or an arylsulphonyl or alkylsulphonyl halide (cf. British Pat. Nos. 1,362,956 and 1,364,125).

Compounds of general formula XA, wherein the various symbols are as hereinbefore defined, may be prepared by reacting a bicyclo-octane derivative of the general formula:

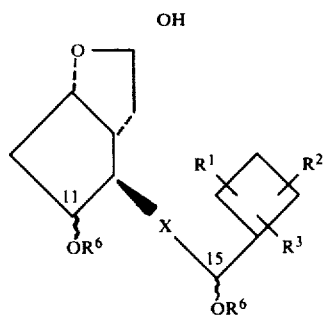

(wherein the various symbols are as hereinbefore defined) with (4-carboxybutylidene)triphenylphosphorane of the formula $\phi_3P{=}CH{-}(CH_2)_3{-}COOH$ (wherein $\phi$ is as hereinbefore defined) to obtain a cyclopentane derivative of the general formula:

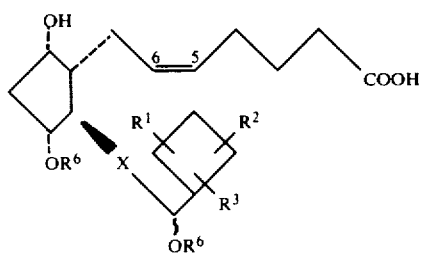

(wherein the various symbols are as hereinbefore defined) and optionally hydrogenating by methods known per se the cis-double bond in the $C_5$–$C_6$ position to obtain a corresponding compound of the general formula:

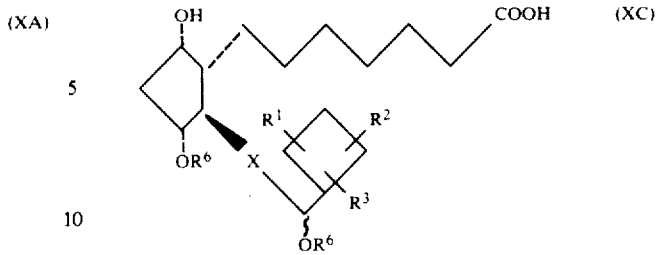

wherein the various symbols are as hereinbefore defined.

If in general formulae XB and XC X represents a trans-vinylene group, mild reducing conditions should be used for the said optional reduction step in order to reduce only the $C_5$–$C_6$ double bond and not to affect the double bond in X. Suitably the reduction may be effected by hydrogenation in the presence of a hydrogenation catalyst, for example palladium on charcoal, in the presence of an inert organic solvent, for example a lower alkanol, e.g. methanol or ethanol, at laboratory temperature at normal or elevated pressure, e.g. at a hydrogen pressure from atmospheric to 15 kilograms per square centimeter. Advantageously the quantity of hydrogen which reacts is observed during the course of the reaction so that the reaction may be terminated before any reduction of X from trans-vinylene to ethylene occurs.

If in general formula XC X represents an ethylene group (X representing in general formula XB either transvinylene or ethylene), then in the said optional reduction step more rigorous reducing conditions may be used, especially if in general formula XB X represents transvinylene, for example hydrogenation in the presence of a hydrogenation catalyst usually used for the hydrogenation of double bonds such as various forms of platinum, palladium or nickel, in a suitable solvent (for example methanol, ethanol, water, dioxan or acetic acid or a mixture of two or more of then), at 0° to 50° C. and at normal or elevated pressure, e.g. at a hydrogen pressure from atmospheric to 15 kilograms per square centimeter.

The reaction between the bicyclo-octane of general formula XV and (4-carboxybutylidene)triphenylphosphorane [obtained by the reaction of sodium methylsulphinylmethylide with (4-carboxybutyl)triphenylphosphonium bromide] is carried out under the normal conditions utilized for effecting the Wittig reaction, e.g. in an inert solvent at ambient temperature. The reaction is preferably carried out in dimethyl sulphoxide because the phosphorane compound is practically insoluble in other solvents, e.g. tetrahydrofuran, and because a cis-double bond must be formed stereospecifically in the Wittig reaction. For the better performance of the Wittig reaction more than two molecular equivalents of the phosphorane compound are required for each mole of the bicyclo-octane reactant. The reaction is generally effected at a temperature of 10°–40° C., preferably at 20°–30° C., and is usually complete after about 30 minutes to four hours at laboratory temperature. The acid product of formula XB may be extracted from the reaction mixture by conventional procedures and further purified by column chromatography on silica gel.

Compounds of general formula XV, wherein the group $OR^6$ attached to the 11-position carbon atom is in α-configuration and the other symbols are as hereinbefore defined [hereinafter depicted in formula XVA], may be prepared from 2-oxa-3-oxo-6R-formyl-7R-acetoxy-cis-bicyclo[3,3,0]octane [E. J. Corey et al., J. Amer. Chem. Soc., 91, 5675 (1969), ibid 92, 397 (1970) and French Patent Application No. 72 15314 (Publication No. 2,134,673)] or 1S-2-oxa-3-oxo-6R-formyl-7R-p-phenylbenzoyloxy-cis-bicyclo[3,3,0]octane [E. J. Corey et al., J. Amer. Chem. Soc., 93, 1491 (1971)] by the series of reactions depicted schematically below in Scheme B:
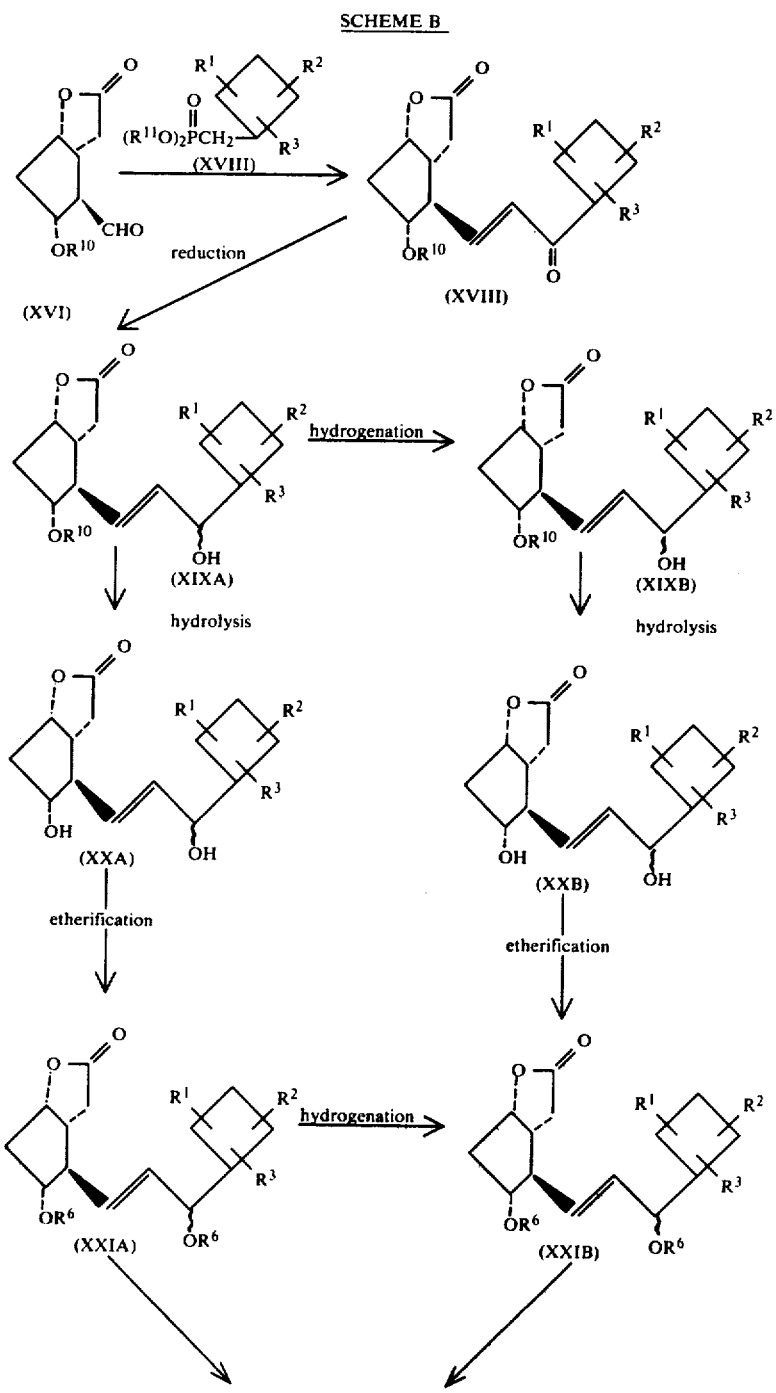

SCHEME B

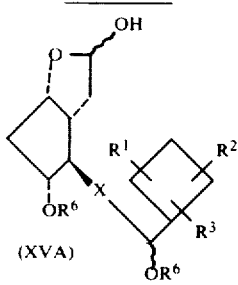

(XVA)

-continued wherein R[10] represents an unsubstituted or substituted acyl (preferably acetyl) group or an unsubstituted or substituted aroyl (preferably p-phenylbenzoyl) group, R[11] represents an alkyl group containing from 1 to 4 carbon atoms, and the other symbols are as hereinbefore defined. Compounds of formula XVI other than the two known compounds referred to above wherein R[10] is acetyl or p-phenylbenzoyl may be prepared by appropriate adaptation of the methods which have been described for the preparation of these known compounds.

The reaction of a compound of general formula XVI with a dialkyl phosphonate of general formula XVII is preferably effected by suspending sodium hydride in an inert organic solvent, e.g. tetrahydrofuran or 1,2-dimethoxyethane, and adding the dialkyl phosphonate of general formula XVII. The resulting sodio derivative of the dialkyl phosphonate may then be reacted with the compound of general formula XVI at a temperature of from 20° C. to 45° C. for one to five hours to form the trans-enone compound of general formula XVIII stereoselectively.

Compounds of general formula XIXA may be prepared by reducing to a hydroxy group the oxo group in the side chain attached to the bicyclo-octane ring of a compound of general formula XVIII. The reduction is suitably effected (1) with excess sodium borohydride in an alcohol containing from 1 to 4 carbon atoms, e.g. methanol, at a low temperature, preferably at −30° C. to −60° C., or (2) with zinc borohydride in a suitable inert organic solvent, e.g. 1,2-dimethoxyethane, at a temperature of −10° C. to 10° C. The product thus obtained is a mixture of isomers in which the hydroxy group is in α- or β-configuration. If desired, the isomer having the hydroxy group in α-configuration may be separated from the isomer having the hydroxy group in β-configuration by column chromatography on silica gel and/or fractional recrystallizations. The separated isomers may be utilized in the procedures herein described to give prostaglandin analogues of general formula VII in which the hydroxy group in position 15 is in α- or β-configuration.

Compounds of general formula XIXA may be catalytically hydrogenated to corresponding compounds of general formula XIXB by means heretofore mentioned for the hydrogenation of compounds of formula XB to those of formula XC.

Compounds of general formulae XXA and XXB may be prepared by hydrolysis under alkaline conditions of compounds of general formulae XIXA and XIXB, respectively, for example by means of anhydrous potassium carbonate in methanol.

Compounds of general formulae XXIA and XXIB may be prepared from compounds of general formulae XXA and XXB, respectively, by reaction with a dihydropyran, dihydrofuran or ethyl vinyl ether in an inert solvent, e.g. methylene chloride, in the presence of a condensing agent, e.g. p-toluenesulphonic acid.

Compounds of general formula XXIA may be catalytically hydrogenated to corresponding compounds of general formula XXIB by means heretofore mentioned for the hydrogenation of compounds of formula XB to those of formula XC.

Compounds of general formula XVA may be prepared by reducing to a hydroxy group the oxo group of compounds of general formulae XXIA and XXIB with diisobutylaluminium hydride in toluene for about 15 minutes at −60° C.

The dialkylphosphonates of general formula XVII may be prepared by reacting a solution of n-butyllithium in an inert organic solvent, e.g. n-hexane, n-pentane or diethyl ether with a solution of a dialkyl methylphosphonate of the general formula:

(XXII)

(wherein R[11] is as hereinbefore defined), e.g. dimethyl methylphosphonate or diethyl methylphosphonate, in an aprotic polar solvent, e.g. THF, at a temperature below −50° C., and then adding dropwise to the reaction mixture a solution of a compound of the general formula:

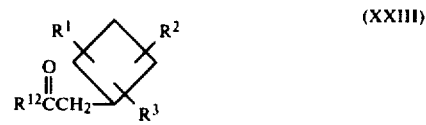

(XXIII)

(wherein R[1], R[2] and R[3] are as hereinbefore defined, and R[12] represents a chlorine atom or a lower alkyl group, preferably containing from 1 to 4 carbon atoms, e.g. methyl or ethyl) in tetrahydrofuran at a temperature below −50° C., stirring the reaction mixture below −50° C., for 1.5 hours and then stirring for 18 hours at 0° C. to give the desired dialkyl phosphonate of general formula XVII.

The compounds of general formula XXIII, e.g. 2,2-propanohexanoyl chloride may be prepared by the methods described in our British Patent Application No. 10560/75, West German Patent Application P 25 10 818.3 and United States Application Ser. No. 557,437 and 2,4-methanoheptanoyl chloride may be prepared by the procedures depicted schematically below:

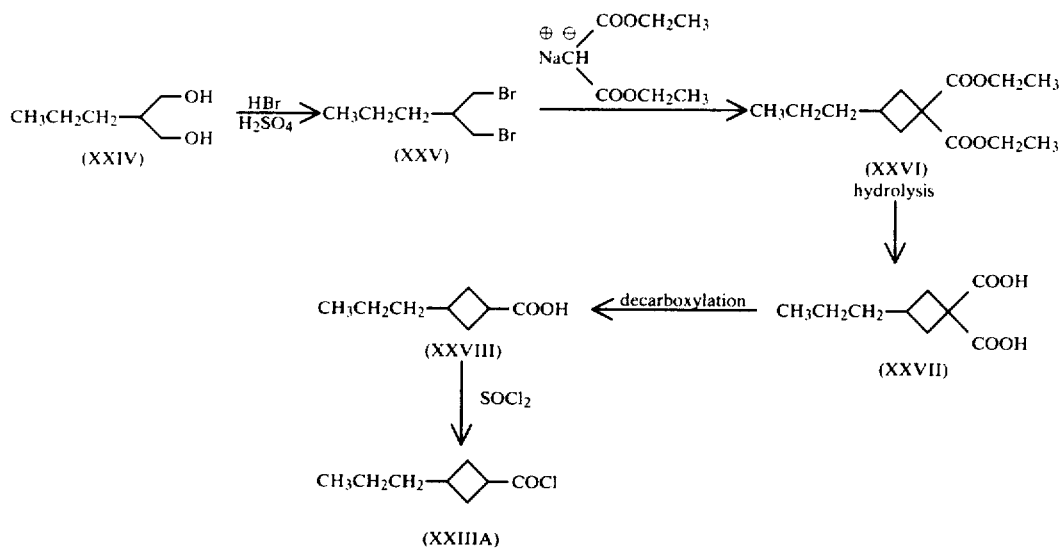

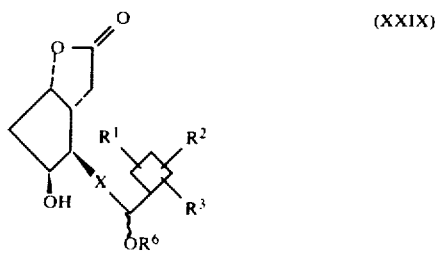

The diol of formula XXIV is treated with 47% (w/v) hydrobromic acid and concentrated sulphuric acid in manner known per se to give the dibromide of formula XXV.

The dibromide of formula XXV is treated with two equivalents of the sodium salt of diethyl malonate to give the compound of formula XXVI, which is hydrolyzed to a compound of formula XXVII.

The cyclobutane carboxylic acid of general formula XXVIII can be obtained by decarboxylation of the compound of formula XXVII. The cyclobutane carboxylic acid of formula XXVIII is treated with thionyl chloride in manner known per se to give the corresponding acid chloride of formula XXIIIA.

The bicyclo-octanes of general formula XV, wherein the group $OR^6$ attached to the 11-position carbon atom is in $\beta$-configuration and the various symbols are as hereinbefore defined may be prepared by etherification of the hydroxy group of a compound of the general formula:

(XXIX)

(wherein the various symbols are as hereinbefore defined) as hereinbefore described for the preparation of compounds of the general formulae XXIA and XXIB from those of general formula XXA and XXB, respectively.

A method for the preparation of the compounds of general formula XXIX wherein the various symbols are as hereinbefore defined, utilizing known procedures may be represented by the series of reactions depicted schematically below in Scheme C (cf. Tetrahedron Letters, 3265–3272, 1972):

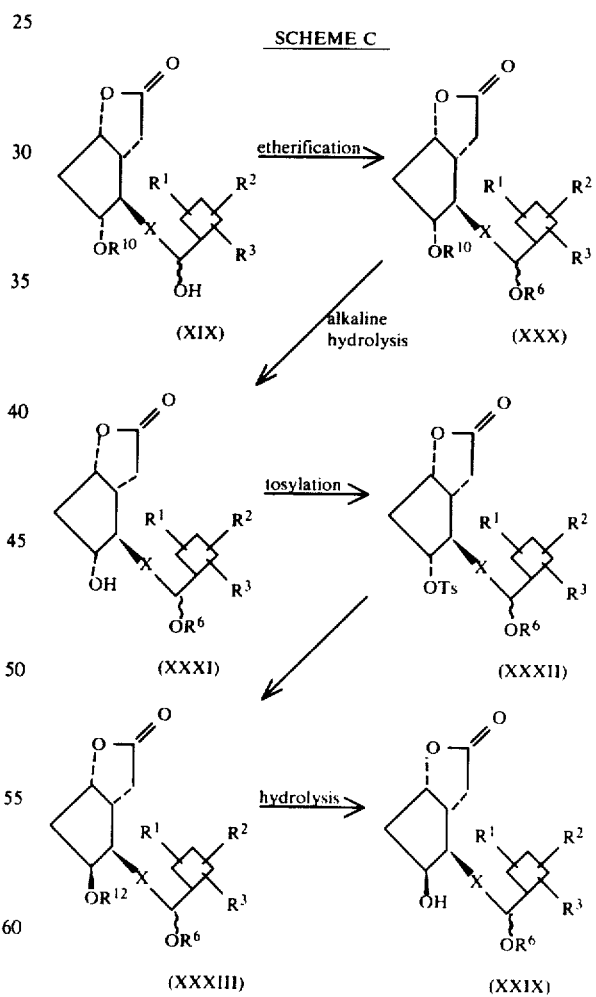

wherein $R^{12}$ represents the formyl group or acetyl group, Ts represents the tosyl group, and the other symbols are as hereinbefore defined. The various reactions may be effected by methods known per se. Compounds of general formula XXXIII may be prepared by reacting compounds of general formula XXXII with tetraethylammonium formate or tetraethylammonium acetate.

If desired, a racemic intermediate of general formula XIX may be separated by column chromatography (cf. Tetrahedron Letters, 3269-3272, 1972) into the isomer in which the hydroxy group is in α-configuration and the isomer in which the hydroxy group is in β-configuration. These isomers of general formula XIX may be utilized in the procedures hereinbefore described to give prostaglandin analogues of formula VII in which the hydroxy group attached to the 15-position carbon atom is in the desired α- or β-configuration.

According to a feature of the present invention the prostaglandin analogues of general formula VII wherein A represents a grouping of formula VIIIA, R represents a group —$CH_2OR^5$ in which $R^5$ represents a hydrogen atom, and the other symbols are as hereinbefore defined, i.e. compounds of the general formula:

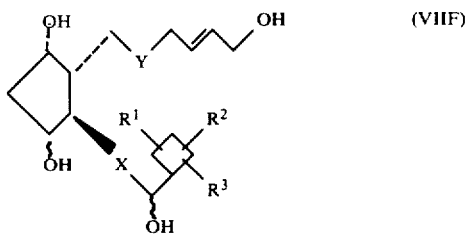

(VIIF)

(wherein the various symbols are as hereinbefore defined) may be prepared by the process which comprises reducing a compound of the general formula:

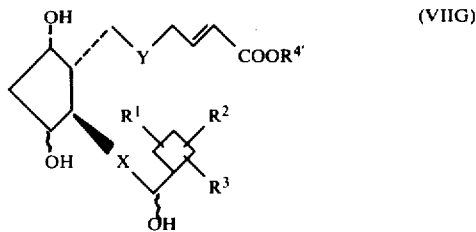

(VIIG)

(wherein $R^{4'}$ represents a straight- or branched-chain alkyl group containing from 1 to 12 carbon atoms and the other symbols are as hereinbefore defined) to convert the group —$COOR^{4'}$ to a hydroxymethyl group by methods known per se for the conversion of a carboxylic ester group to a hydroxymethyl group. The reduction is preferably effected, for example, by treating the compound of general formula VIIG with 6 to 10 molecular equivalents of diisobutylaluminium hydride in an inert organic solvent, e.g. toluene or tetrahydrofuran, at a low temperature, e.g. −78° C.

According to a further feature of the invention compounds of general formula VII wherein A represents a grouping of formula VIIIA, R represents a group —$CH_2OR^5$ in which $R^5$ represents an alkylcarbonyl group containing from 2 to 5 carbon atoms, and the other symbols are as hereinbefore defined, i.e. compounds of the general formula:

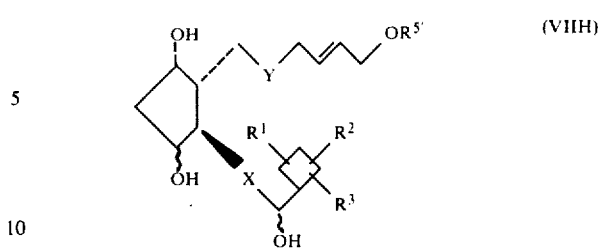

(VIIH)

(wherein $R^{5'}$ represents an alkylcarbonyl group containing from 2 to 5 carbon atoms and the other symbols are as hereinbefore defined) may be prepared from compounds of general formula VIIF, wherein the various symbols are as hereinbefore defined, by selective acylation under mild conditions, for example, with an equimolecular amount of an acyl halide in the presence of pyridine in an inert organic solvent, e.g. methylene chloride, at a low temperature, e.g. −20° to −10° C.

According to a further feature of the present invention compounds of general formula VII, wherein A represents a grouping of formula VIIIB, R represents a group —$CH_2OR^{5'}$, in which $R^{5'}$ is as hereinbefore defined, and the other symbols are as hereinbefore defined, i.e. compounds of the general formula:

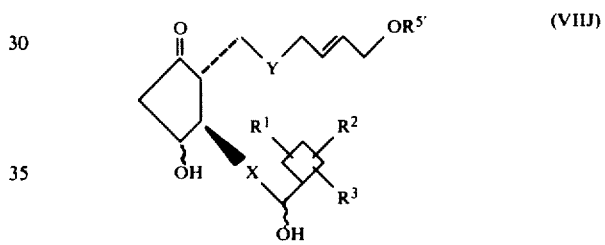

(VIIJ)

(wherein the various symbols are as hereinbefore defined) may be prepared from compounds of general formula VII, wherein A represents a grouping of formula VIIIB, R represents a group —$CH_2OR^5$, in which $R^5$ represents hydrogen, and the other symbols are as hereinbefore defined, i.e. compounds of the general formula:

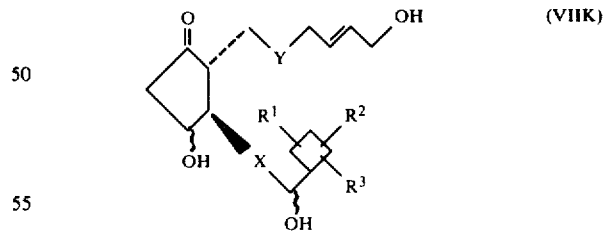

(VIIK)

(wherein the various symbols are as hereinbefore defined) by means heretofore mentioned for the conversion of compounds of general formula VIIF to those of general formula VIIH.

According to a further feature of the present invention compounds of general formula VIIK, wherein the various symbols are as hereinbefore defined, may be prepared from compounds of the general formula XXXVI depicted hereafter in Scheme D (wherein $R^{13}$ represents the trityl group, i.e. —$C\phi_3$, wherein $\phi$ represents the phenyl group, and the other symbols are as hereinbefore defined) by means heretofore mentioned for the conversion of compounds of formula IX to those of formula VIIB. The group $OR^{13}$ is converted to a hydroxy group under the conditions used to hydrolyse to hydroxy groups the groups $OR^6$.

Compounds of general formula XXXVI (wherein the various symbols are as hereinbefore defined) may be prepared from compounds of general formula IX, wherein Z represents

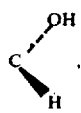

$R^4$ represents a straight- or branched-chain alkyl group containing from 1 to 12 carbon atoms, and the other symbols are as hereinbefore defined, i.e. compounds of the general formula:

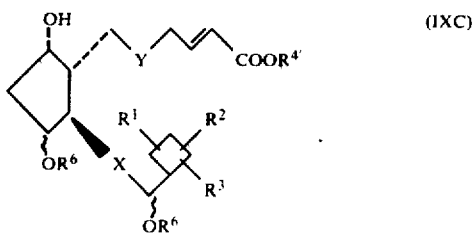

(IXC)

(wherein the various symbols are as hereinbefore defined) as depicted schematically below in Scheme D.

The preparation of compounds of general formulae VIIJ and VIIK, and of compounds of general formula XXXVI may be represented by the series of reactions depicted schematically below in Scheme D, wherein the various symbols are as hereinbefore defined.

SCHEME D

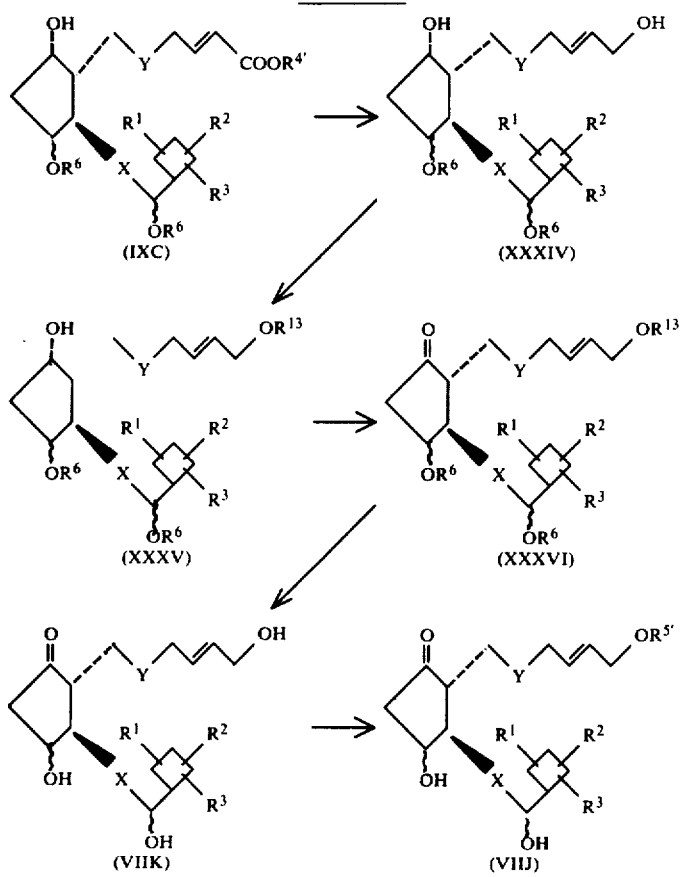

The conversion of compounds of general formula IXC to those of general formula XXXIV may be carried out by means heretofore mentioned for the conversion of compounds of general formula VIIG to those of general formula VIIF. Compounds of general formula XXXIV may be converted to compounds of general formula XXXV by reaction with trityl chloride in pyridine or in methylene chloride in the presence of a base, e.g. pyridine or a tertiary amine, at a temperature ranging from ambient to 70° C.

The conversion of compounds of general formula XXXV to compounds of general formula XXXVI may be effected as hereinbefore described for the conversion of compounds of general formula IXA to IXB.

Compounds of general formulae VIIK and VIIJ may be converted to the corresponding PGA compounds of general formula VII, wherein A represents a grouping of formula IV, by means heretofore mentioned for the conversion of compounds of general formula VIID to those of general formula VIIE.

According to a further feature of the present invention, the compounds of general formula VII, wherein R represents a group $—COOR^4$, in which $R^4$ represents a straight- or branched-chain alkyl group containing from 1 to 12 carbon atoms, and the other symbols are as hereinbefore defined are prepared by esterification of the corresponding acids of formula VII wherein $R^4$ represents a hydrogen atom by methods known per se, for example by reaction with (i) the appropriate diazoalkane in an inert organic solvent, e.g. diethyl ether, at a temperature of from $-10°$ C. to $25°$ C. and preferably $0°$ C., (ii) the appropriate alcohol in the presence of dicyclohexylcarbodiimide as condensing agent, or (iii) the appropriate alcohol following formation of a mixed anhydride by adding a tertiary amine and pivaloyl halide or an arylsulphonyl or alkylsulphonyl halide (cf. British Pat. Nos. 1,362,956 and 1,364,125).

Compounds of general formula VII wherein R represents a group $COOR^4$, in which $R^4$ represents a hydrogen atom may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acid are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of general formula VII wherein R represents a group $COOR^4$, in which $R^4$ represents a hydrogen atom by, for example, reaction of stoichiometric quantities of an acid of general formula VII and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of general formula VII may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the prostaglandin analogues.

The prostaglandin analogues of general formula VII and their cyclodextrin clathrates and, when R represents a group $COOR^4$, in which $R^4$ represents a hydrogen atom, non-toxic salts thereof possess the valuable pharmacological properties typical of the prostaglandins in a selective fashion, including, in particular, hypotensive activity, inhibitory activity on blood platelet aggregation, coronary vasodilator activity, stimulatory activity on uterine contraction and abortifacient activity and are useful in the treatment of hypertension, in the treatment of *angina pectoris* and in the prevention and treatment of cerebral thrombosis and myocardial infarction, and more especially in the termination of pregnancy and induction of labour in pregnant female mammals and in the control of conception and menstral regulation in female mammals.

The preferred compounds of the invention in respect of their inhibitory activity on blood platelet aggregation are 16,18-methano-20-methyl-trans-2,3-didehydro-$PGE_1$ and its methyl ester, and the preferred compound of the invention in respect of its coronary vasodilator activity is 16,18-methano-20-methyl-trans-2,3-didehydro-$PGE_1$. 16,18-Methano-20-methyl-trans-2,3-didehydro-$PGE_1$ is particularly preferred in respect of these properties. For example, in laboratory screening tests, 16,18-methano-20-methyl-trans-2,3-didehydro-$PGE_1$
(a) produces a 24 mmHg fall for 6 minutes and a 68 mmHg fall for 11 minutes in the blood pressure of the allobarbital-anaesthetized dog by intravenous administration at doses of 1.0 and 2.0 $\mu$g/kg animal body weight, respectively; (b) produces 50% inhibition of adenosine diphosphate-induced blood platelet aggregation in platelet-rich plasma of rats and humans at doses of $6.1 \times 10^{-4}$ $\mu$g/ml and $1.85 \times 10^{-4}$ $\mu$g/ml, respectively; and (c) is 21 times as potent as $PGE_1$ in increasing the coronary flow in rabbit isolated hearts. 16,18-Methano-20-methyl-trans-2,3-didehydro-$PGE_1$ methyl ester (a) produces a 20 mmHg fall for 9 minutes and a 52 mmHg fall for 10 minutes in the blood pressure of the allobarbital-anaesthetized dog by intravenous administration at doses of 1.0 and 2.0 $\mu$g/kg animal body weight, respectively; and (b) produces a $40 \pm 14.4$ mmHg fall at 0.5 hours, a $17 \pm 17.4$ mmHg fall at 1 hour and a $22 \pm 6.7$ mmHg fall at 3 hours after administration in the blood pressure of the conscious spontaneously hypertensive rat by oral administration at a dose of 1.0 mg/kg animal body weight.

The preferred compounds of the invention in respect of their stimulatory activity on uterine contraction are 16,16-propano-trans-2,3-didehydro-$PGE_1$ and its methyl ester. For example, in laboratory screening tests, 16,16-propano-trans-2,3-didehydro-$PGE_1$ and its methyl ester stimulate uterine contraction in the pregnant female rat when administered intravenously on the 20th day of gestation at a dose of 0.20 $\mu$g and are 100-200 times as potent as $PGF_{2\alpha}$ (i.e. 10-20 times as potent as $PGE_1$).

The prostaglandin analogues of the present invention and their cyclodextrin clathrates and non-toxic salts exhibit the aforesaid valuable properties at doses which do not, in general, induce diarrhoea as an undesired side-effect. For example, the doses by oral administration of 16,18-methano-20-methyl-trans-2,3-didehydro-$PGE_1$ and its methyl ester, and 16,16-propano-trans-2,3-didehydro-$PGE_1$ and its methyl ester required to induce diarrhoea in 50% of mice so treated are $>20$ and $>20$ mg/kg animal body weight, and 0.85 and 0.90 mg/kg animal body weight, respectively.

The pharmacological activities of 16,18-methano-20-methyl-trans-2,3-didehydro-$PGE_1$ and its methyl ester, and of 16,16-propano-trans-2,3-didehydro-$PGE_1$ and its methyl ester are summarised in the following Table, in which the potencies are expressed relative to $PGE_1 = 1$ or $PGF_{2\alpha} = 1$.

|  | Inhibitory activity on blood platelet aggregation | | Coronary vasodilator activity rabbit isolated | Stimulatory activity on uterine contraction | Production of diarrhoea |
|---|---|---|---|---|---|
|  | Human $PGE_1 = 1$ | rat $PGE_1 = 1$ | heart $PGE_1 = 1$ | rat $PGF_{2\alpha} = 1$ ($PGE_1 = 1$) | mice $PGE_1 = 1$ |
| 16,16-propano-trans-2,3-didehydro-PGE$_1$ | | | 1.5 | 100–200 (10–20) | 27 |
| 16,16-propano-trans-2,3-didehydro-PGE$_1$ methyl ester | | | 0.80 | 100–200 (10–20) | 26 |
| 16,18-methano-20-methyl-trans-2,3-didehydro-PGE$_1$ | 50 | 30 | 21 | | <1 |
| 16,18-methano-20-methyl-trans-2,3-didehydro-PGE$_1$ methyl ester | 50 | | | 2–5 (0.2–0.5) | <1 |

As will be noted from the Table, 16,16-propano-trans-2,3-didehydro-PGE$_1$ and its methyl ester produce strong desirable effects (stimulatory activity on uterine contraction). Moreover, 16,16-propano-trans-2,3-didehydro-PGE$_1$ and its methyl ester have relatively low potencies in inducing diarrhoea in comparison with their potencies in respect of the valuable pharmacological properties hereinbefore mentioned. These data indicate that 16,16-propano-trans-2,3-didehydro-PGE$_1$ and its methyl ester have a very strong stimulatory activity on uterine contraction, making the compounds particularly useful in the termination of pregnancy and induction of labour and in the control of conception and menstrual regulation.

16,18-Methano-20-methyl-trans-2,3-didehydro-PGE$_1$ also produces strong desirable effects (inhibitory activity on blood platelet aggregation and coronary vasodilator activity) and has relatively low potency in inducing diarrhoea in comparison with its potency in respect of the valuable pharmacological properties hereinbefore mentioned. These data indicate that 16,18-methano-20-methyl-trans-2,3-didehydro-PGE$_1$ has a strong inhibitory activity on blood platelet aggregation and coronary vasodilator activity making the compound particularly useful in the prevention and treatment of cerebral thrombosis and myocardial infarction and in the treatment of *angina pectoris*.

Preferred compounds of the invention are those compounds of general formula VII wherein A represents a grouping of formula VIIIB, Y represents ethylene, X represents trans-vinylene, R represents a group COOR$^4$, in which R$^4$ represents hydrogen or methyl, R$^1$ represents n-propyl or n-butyl and R$^2$ and R$^3$ represent hydrogen.

Compounds of general formulae IX and XXXVI, wherein the various symbols are as hereinbefore defined, are new and as such, constitute further features of the present invention.

The following Reference Examples and Examples illustrate the process of the present invention and products thereof. In the Examples, 'IR', 'NMR' and 'TLC' represent respectively 'Infrared absorption spectrum', 'Nuclear magnetic resonance spectrum' and 'Thin layer chromatography'. Where solvent ratios are specified in chromatographic separations the ratios are by volume.

REFERENCE EXAMPLE 1

2-n-Propyl-1,3-dibromopropane

To a solution of 2-n-propylpropane-1,3-diol (60.0 g., 0.508 mol) in a mixture of 47% hydrobromic acid (211 g., 1.22 mol) and sulphuric acid (63.5 g., 0.65 mol) was added sulphuric acid (103 g., 1.04 mol). The reaction mixture was refluxed for 16 hours and then subjected to steam distillation. The water-insoluble layer of distillates was separated, washed with water (15 ml.) and an aqueous solution of sodium carbonate (15 ml.), dried over calcium chloride and then distilled (20 mm.Hg., 105° C.–110° C.) to give 104 g. of the title compound (84% yield) having the following physical characteristics:

b.p.: 105° C.–110° C. (20 mm.Hg);

NMR (CCl$_4$): δ; 3.67-3.30 (4H, multiplet), 2.10-1.80 (1H, multiplet), 1.60-1.18 (4H, multiplet), 1.10-0.84 ppm (3H, multiplet);

IR (liquid film): ν; 1460, 1255, 1240, 1210 cm$^{-1}$;

Mass spectrum: m/e=246 (M$^+$ +4), 244 (M$^+$ +2), 242 (M$^+$), 163, 83.

REFERENCE EXAMPLE 2

3-n-Propylcyclobutane-1,1-dicarboxylic acid diethyl ester

Diethyl malonate (96.0 g., 0.608 mol) was added to sodium ethoxide solution [prepared by the addition of 13.8 g. (0.6 gram atom) of sodium to 300 ml. of absolute ethanol] and the mixture was refluxed with stirring. Over a period of one hour, sodium ethoxide solution [prepared by the addition of 12.2 g. (0.5 gram atom) of sodiumto 200 ml. of absolute ethanol] and 2-n-propyl-1,3-dibromopropane (12.2 g., 0.5 mol, prepared as described in Reference Example 1) were added concurrently to the boiling reaction mixture. After the addition was completed, the mixture was refluxed with stirring for 2 hours, and then 400 ml. of ethanol was distilled from the reaction mixture. The residue was mixed with water and extracted with benzene (5×300 ml.). After concentration of the extracts under reduced pressure, a crude product was obtained, which was distilled in vacuo to give the title compound in 84% yield. This compound had the following physical characteristics:

b.p.: 91° C.–110° C./1 mm.Hg;

NMR (CCl$_4$): δ; 4.20-4.00 (4H, multiplet), 1.35-1.17 (6H, multiplet), 1.03-0.75 ppm (3H, multiplet);

IR (liquid film): ν; 1730, 1270, 1140 cm$^{-1}$;

Mass spectrum: m/e 242 (M$^+$).

REFERENCE EXAMPLE 3

3-n-Propylcyclobutane-1,1-dicarboxylic acid

A solution of 3-n-propylcyclobutane-1,1-dicarboxylic acid diethyl ester (100 g., 0.413 mol, prepared as described in Reference Example 2) in benzene (200 ml.) was treated with sodium hydroxide (320 g., 8.00 mol) in water (400 mol.) for 20 hours at room temperature. The reaction mixture was acidified with 6 N hydrochloric acid and extracted with diethyl ether (3×400 ml.). After concentration of the extracts under reduced pressure, the resulting crude solid was recrystallized from chloroform to give the title compound in quantitative yield, having the following physical characteristics:

NMR (CD$_3$OD): δ; 6.30-5.30 (2H, D$_2$O exchanged), 1.05-0.75 ppm (3H, multiplet);

IR (KBr): ν; 3500-2300, 1700 cm$^{-1}$;

Mass spectrum: m/e 186 (M+).

REFERENCE EXAMPLE 4

2,4-Methanoheptanoic acid 3-n-Propylcyclobutane-1,1-dicarboxylic acid (45.0 g., 0.242 mol, prepared as described in Reference Example 3) was kept at 175° C. for 20 hours. The oily crude product was distilled under reduced pressure to give in almost quantitative yield the title compound having the following physical characteristics:

b.p.: 138° C.-139.8° C./20 mm.Hg;

NMR (CCl$_4$): δ; 12.05 (1H, D$_2$O exchanged), 3.25-2.75 (1H, multiplet), 1.05-0.75 ppm (3H, multiplet);

IR (liquid film): ν; 3500-2200, 1700 cm$^{-1}$;

Mass spectrum: m/e=143 (M+).

REFERENCE EXAMPLE 5

2,4-Methanoheptanoyl chloride

Freshly distilled thionyl chloride (50 ml.) was added to 2,4-methanoheptanoic acid (14.3 g., prepared as described in Reference Example 4). After stirring for 1.5 hours at room temperature, the temperature of the reaction mixture was raised to 75° C. and kept at that temperature for 2 hours. After removal of thionyl chloride under reduced pressure, the oily residue was distilled in vacuo to give 2,4-methanoheptanoyl chloride in quantitative yield, having the following physical characteristics:

b.p.: —48° C./1 mm.Hg;

IR (liquid film): ν; 1800 cm$^{-1}$.

REFERENCE EXAMPLE 6

Dimethyl 2-oxo-3,5-methanooctylphosphonate

A solution of dimethyl methylphosphonate (29.8 g., 0.240 mol) in tetrahydrofuran (150 ml.) was treated with n-butyllithium (0.240 mol) in hexane (1 equivalent relative to the phosphonate) for 40 minutes at —70° C. under an atmosphere of nitrogen. The reaction mixture was further treated with 2,4-methanoheptanoyl chloride (15.4 g., prepared as described in Reference Example 5) in tetrahydrofuran (150 ml.) for 80 minutes at —70° C. After stirring for 50 minutes at —70° C. and for 1.5 hours at room temperature, the reaction mixture was worked up in the following manner: The reaction mixture was acidified with glacial acetic acid (10 ml.), and then concentrated under reduced pressure. The residue was dissolved in water (25 ml.) and extracted with diethyl ether (5×100 ml.). The combined organic layers were dried over magnesium sulphate, concentrated and distilled in vacuo to give 18.3 g. (yield 76.9%) of dimethyl 2-oxo-3,5-methanooctylphosphonate having the following physical characteristics:

b.p.: 130° C.-133° C./1 mm.Hg;

NMR (CDCl$_3$): δ; 3.78 (6H, doublet, J=11.0 Hz), 3.29-2.91 (2H, multiplet), 2.50-1.00 (10H, multiplet), 0.98-0.75 ppm (3H, multiplet);

IR (liquid film): ν; 1710, 1260, 1040 cm$^{-1}$;

Mass spectrum: m/e 248 (M+), 205 (M+ —43), 178 (M+ —70), 151 (M+ —97), 109 (M+ —139).

REFERENCE EXAMPLE 7

1S-2-Oxa-3-oxo-6R-(3-oxo-4,6-methanonon-trans-1-enyl)-7R-acetoxy-cis-bicyclo[3,3,0]octane Anhydrous pyridine (32.6 ml.) and chromium trioxide (19.8 g., 198 mmol) were added to methylene chloride (530 ml.) at 10°-20° C., and stirred for 15 minutes. The reaction mixture was treated with Celite 545 (37.5 g.) and cooled to 0° C. 1S-2-oxa-3-oxo-6R-hydroxymethyl-7R-acetoxy-cis-bicyclo[3,3,0]octane (8.00 g., 37.4 mmol) [prepared as described in J. Amer. Chem. Soc., 92, 397 (1970)] in methylene chloride (85 ml.) was oxidized using the chromium trioxide solution (prepared as described above) with stirring for 15 minutes at 0° C. After addition of sodium bisulphate monohydrate (145 g.), the mixture was stirred for an additional 10 minutes and then filtered through a pad of magnesium sulphate at 0° C. After washing the solids with cold methylene chloride, the solution was concentrated using a rotary evaporator (0° C.) to afford the crude aldehyde, which was used immediately in the next step.

To a suspension of sodium hydride (1.54 g., 41.6 mmol) in 1,2-dimethoxyethane was added a solution of dimethyl 2-oxo-3,5-methanooctylphosphonate (10.3 g., 41.6 mmol, prepared as described in Reference Example 6) in 1,2-dimethoxyethane (200 ml.). The mixture was stirred at room temperature for 30 minutes, by which time no further hydrogen was evolved. To the reaction mixture was added the crude aldehyde (obtained as described above) in 1,2-dimethoxyethane (200 ml.) at 3°-5° C., and the mixture was stirred at room temperature for 40 minutes. After neutralizing excess base with glacial acetic acid, the solvent was removed under reduced pressure. The residue was dissolved in water and extracted with ethyl acetate. The organic layer was washed with water, dried over magnesium sulphate, and concentrated to give a product. The oily product was chromatographed on silica gel using a mixture of benzene and ethyl acetate (8:1) as eluant to yield the title compound (5.30 g.) in a yield of 42.4% based on 1S-2-oxa-3-oxo-6R-hydroxymethyl-7R-acetoxy-cis-bicyclo[3,3,0]octane, having the following physical characteristics:

NMR (CDCl$_3$): δ; 6.75-6.45 (1H, multiplet), 6.23-6.00 (1H, multiplet, 5.15-4.90 (2H, multiplet), 2.03 (3H, singlet), 0.98-0.75 ppm (3H, multiplet);

IR (CHCl$_3$): ν; 1775, 1740, 1690, 1660, 1630, 1240, 1070, 990 cm$^{-1}$;

Mass spectrum: m/e=334 (M+), 274 (M+ —60).

REFERENCE EXAMPLE 8

1S-2-oxa-3-oxo-6R-[3R(and 3S)-hydroxy-4,6-methanonon-trans-1-enyl]-7R-acetoxy-cis-bicyclo[3,3,0]octane To a solution of 1S-2-oxa-3-oxo-6R-(3-oxo-4,6-methanonon-trans-1-enyl)-7R-acetoxy-cis-bicyclo[3,3,-0]octane (7.6 g., 23 mmol, prepared as described in Reference Example 7) in absolute methanol (160 ml.) and anhydrous tetrahydrofuran (80 ml.) was gradually added sodium borohydride (3.78 g., 100 mmol) at −30° C. After stirring for 15 minutes, the reaction mixture was quenched by addition of glacial acetic acid (13 ml.), and concentrated. The residue was dissolved in water and the solution extracted with chloroform.

The extract was dried over sodium sulphate and concentrated to yield an oily product (7.8 g.). After removal of excess acetic acid in vacuo, the crude residue was purified by column chromatography on silica gel (800 g.) using a mixture of diethyl ether and hexane (8:2) as eluant. The following fractions were collected.

(a) 3.1 g. (desired 3S-alcohol)
(b) 2.1 g. (mixture of 3R- and 3S-alcohols)
(c) 2.4 g. (3R-alcohol)

The fraction (b) was further purified by additional column chromatography on silica gel (200 g.) to yield (d) 0.60 g. (3S-alcohol), (e) 0.89 g. mixture of (3R- and 3S-alcohols) and (f) 0.46 g. (3R-alcohol).

(1) 3S-alcohol has the following physical characteristics:

NMR (CDCl$_3$): δ; 5.58-5.45 (2H, multiplet), 5.05-4.85 (2H, multiplet), 4.10-3.80 (1H, multiplet), 2.02 (3H, singlet), 0.98-0.75 ppm (3H, multiplet);

IR (CHCl$_3$): ν; 3500, 1780, 1770, 1740, 1730, 1250, 980 cm$^{-1}$;

Mass spectrum: m/e = 276 (M$^+$ −60), 249 (M$^+$ −97), 179 (M$^+$ −157);

Optical rotation: $[\alpha]_D^{22}$ = −10.5° (c = 1.04 CHCl$_3$).

(2) 3R-alcohol has the following physical characteristics:

NMR (CDCl$_3$): 5.58-5.45 (2H, multiplet), 5.08-4.85 (2H, multiplet), 4.10-3.80 (1H, multiplet), 2.02 (3H, singlet), 0.98-0.75 ppm (3H, multiplet);

IR (CHCl$_3$): ν; 3450, 1770, 1740, 1240, 975 cm$^{-1}$;

Mass spectrum: m/e = 276 (M$^+$ −60), 179 (M$^+$ −157);

Optical rotation: $[\alpha]_D^{22}$ = −42.4° (c = 1.10, CHCl$_3$); m.p.: 87° C.-90° C.

REFERENCE EXAMPLE 9

1S-2-oxa-3-oxo-6R-(3S-hydroxy-4,6-methanonon-trans-1-enyl)-7R-hydroxy-cis-bicyclo[3,3,0]octane A heterogeneous mixture of 1S-2-oxa-3-oxo-6R-(3S-hydroxy-4,6-methanonon-trans-1-enyl)-7R-acetoxy-cis-bicyclo[3,3,0]octane (3.10 g., 9.23 mol, prepared as described in Reference Example 8), finely powdered anhydrous potassium carbonate (1.33 g., 9.64 mmol) and methanol (35 ml.) was vigorously stirred at room temperature for 15 minutes and then cooled in an ice bath. After addition of 1.0 N hydrochloric acid (17.1 ml.), the reaction mixture was extracted with chloroform. The organic layer was washed with a saturated aqueous solution of sodium chloride, and concentrated by rotary evaporation to afford an oily product. The crude product was purified by short column chromatography on silica gel using benzene, followed by a mixture of chloroform and ethanol (8:1), as eluant to give 2.60 g. (yield 95.8%) of the title compound having the following physical characteristics:

NMR (CDCl$_3$): δ; 5.55-4.90 (2H, multiplet), 5.05-4.76 (1H, multiplet), 4.10-3.75 (2H, multiplet), 0.98-0.75 ppm (3H, multiplet);

IR (CHCl$_3$): ν; 3400, 1765, 975 cm$^{-1}$;

Mass spectrum: m/e = 295 (M$^-$ +1), 294 (M$^+$), 277 (M$^-$ −17), 276 (M$^-$ −18), 258 (M$^-$ −36);

Optical rotation: $[\alpha]_D^{18}$ = +0.27° (c = 2.61, CHCl$_3$).

REFERENCE EXAMPLE 10

1S-2-oxa-3-oxo-6R-(3S-tetrahydropyran-2'-yloxy-4,6-methanonon-trans-1-enyl)-7R-tetrahydropyran-2'-yloxy-cis-bicyclo[3,3,0]octane A solution of 1S-2-oxa-3-oxo-6R-(3S-hydroxy-4,6-methanonon-trans-1-enyl)-7R-hydroxy-cis-bicyclo[3,3,0]octane (2.46 g., 8.37 mmol, prepared as described in Reference Example 9), p-toluenesulphonic acid (10 mg.) and freshly distilled 2,3-dihydropyran (7.5 ml.) in methylene chloride (30 ml.) was stirred for 15 minutes at room temperature. The reaction was quenched by addition of 7 drops of pyridine and the mixture was diluted with chloroform. After washing with a saturated aqueous solution of sodium chloride, the organic layer was dried over sodium sulphate and concentrated to yield 4.20 g. (3.87 g. calculated; polymers derived from dihydropyran could be involved as impurity) of the title compound as a colourless oil. The crude product was used without purification in Reference Example 11 described hereinafter and has the following physical characteristics:

NMR (CDCl$_3$): δ; 5.65-5.20 (2H, multiplet), 5.05-4.80 (1H, multiplet), 4.75-4.50 (2H, multiplet), 4.10-3.70 -4H, multiplet), 3.62-3.30 (2H, multiplet), 0.98-0.75 ppm (3H, multiplet);

IR (CHCl$_3$): ν; 1765, 1180, 1130, 1075, 1035, 1020, 975 cm$^{-1}$;

Mass spectrum: m/e 363 (M$^+$ −99), 362 (M$^+$ −100), 276 (M$^+$ −186) 258 (M$^+$ −204);

Optical rotation $[\alpha]_D^{23}$ = −28.2° (c = 1.12, CHCl$_3$).

REFERENCE EXAMPLE 11

1S-2-oxa-3ξ-hydroxy-6R-(3S-tetrahydropyran-2'-yloxy-4,6-methanonon-trans-1-enyl)-7R-tetrahydropyran-2'-yloxy-cis-bicyclo[3,3,0]octane To a stirred cold solution (−70° C.) of the crude 1S-2-oxa-3-oxo-6R-(3S-tetrahydropyran-2'-yloxy-4,6-methanonon-trans-1-enyl)-7R-tetrahydropyran-2'-yloxy-cis-bicyclo[3,3,0]octane (3.87 g., 8.39 mol, prepared as described in Reference Example 10) in toluene (60 ml.) was added dropwise 8.9 ml. of a solution of diisobutylaluminium hydride (25 g.) in toluene (100 ml.). The homogeneous solution was stirred for 20 minutes at −70° C., and then quenched by addition of methanol (16.5 ml.). After stirring for 15 minutes at room temperature, and then dilution with diethyl ether, the ethereal solution was washed with a saturated aqueous solution of sodium bitartrate. The ethereal solution was dried over magnesium sulphate and concentrated to yield the title compound, which was used immediately without purification in Reference Example 12 described hereinafter, having the following physical characteristics:

NMR (CDCl$_3$): δ; 5.70-5.10 (2H, multiplet), 4.78-4.40 (3H, multiplet), 4.13-3.25 (7H, multiplet), 0.98-0.75 ppm (3H, multiplet);

IR (CHCl$_3$): ν; 3400, 1130, 1075, 1020, 1000, 975, 905, 870 cm$^{-1}$;

Mass spectrum: m/e 362 (M$^+$ −86), 344 (M$^+$ −104), 244 (M$^+$ −204).

REFERENCE EXAMPLE 12

9S-Hydroxy-11R,15S-bis(2-tetrahydropyranyloxy)-16,18-methano-20-methylprosta-cis-5,trans-13-dienoic acid Sodium methylsulphinylmethylide was prepared as follows: A mixture of sodium hydride (359 mg.) and anhydrous dimethyl sulphoxide (48 ml.) was stirred at 60° C. until gas evolution ceased (ca. 2-3 hours). After cooling to room temperature the solution was ready for use. The anhydrous dimethyl sulphoxide was prepared by drying same and distilling over calcium hydride.

To a solution of (4-carboxybutyl)triphenylphosphonium bromide (13.0 g.) in anhydrous dimethyl sulphoxide (30 ml.) was added 35.2 ml. (71.0 mmol) of sodium methylsulphinylmethylide solution in dimethyl sulphoxide (obtained as described in the preceding paragraph) with stirring to give a red solution to which, after a further 5 minutes stirring, a solution of the 1S-2-oxa-3ξ-hydroxy-6R-(3S-tetrahydropyran-2'-yloxy-4,6-methanonon-trans-1-enyl)-7R-tetrahydropyran-2'-yloxy-cis-bicyclo[3,3,0]octane (3.87 g., prepared in Reference Example 11) in dimethyl sulphoxide (30 ml.) was added. The reaction mixture was stirred at 25° C.±1° C. for 30 minutes, at 30° C. for an additional 2 hours, and then quenched with ice-water. The reaction mixture was diluted with a mixture of ethyl acetate and diethyl ether (1:1), and then shaken with an aqueous solution of potassium carbonate, after which the pH of the solution was about 10. After confirming by TLC that no product was present in the organic layer, the aqueous layer was acidified to pH 2-3 with 1.0 N hydrochloric acid and extracted with a mixture of pentane and diethyl ether (1:1).

The acidic extracts were dried over magnesium sulphate and concentrated to yield 3.50 g. of an oily product. The oily product was purified by column chromatography on silica gel (100 g.) using a mixture of chloroform and ethanol (40:1) as eluant to give 2.88 g. [yield 62.8% based on 1S-2-oxa-3-oxo-6R-(3S-hydroxy-4,6-methanonon-trans-1-enyl)-7R-hydroxy-cis-bicyclo[3,3,-0]octane] of the title compound as a pure oily product having the following physical characteristics:

NMR (CDCl$_3$); δ: 5.70-5.05 (5H, multiplet), 4.83-4.55 (2H, multiplet), 4.25-3.70 (2H, multiplet), 3.65-3.30 (2H, multiplet), 0.98-0.75 ppm (3H, multiplet);

IR (CHCl$_3$): ν; 3600-2400, 1710, 1130, 1075, 1020, 970, 900, 865 cm$^{-1}$;

Mass spectrum: m/e=374 (M$^+$ −174), 362 (M$^+$ −186), 344 (M$^+$ −204);

Optical rotation: $[\alpha]_D^{18}$= +10.4° (c=2.09, CHCl$_3$).

REFERENCE EXAMPLE 13

Methyl 9S-hydroxy-11R,15S-bis(2-tetrahydropyranyloxy)-16,18-methano-20-methylprosta-cis-5,trans-13-dienoate A solution of 9S-hydroxy-11R,15S-bis(2-tetrahydropyranyloxy)-16,18-methano-20-methylprosta-cis-5,trans-13-dienoic acid (900 mg., 1.64 mmol, prepared as described in Reference Example 12) in methanol (10 ml.) was treated with excess diazomethane in diethyl ether. After stirring for a few minutes, the reaction mixture was concentrated. The residue was purified by column chromatography on silica gel (25 g.) using a mixture of benzene and ethyl acetate (5:1) as eluant to give 759 mg. (yield 82.3%) of the title compound as a pure oily product having the following physical characteristics:

NMR (CDCl$_3$): δ; 5.65-5.10 (4H, multiplet), 4.80-4.60 (2H, multiplet), 4.20-3.70 (5H, multiplet), 3.66 (3H, singlet), 3.60-3.32 (2H, multiplet), 0.98-0.75 ppm (3H, multiplet);

IR (CHCl$_3$): ν; 3500, 1730, 1440, 1130, 1080, 1020, 1000, 980, 905, 870 cm$^{-1}$;

Mass spectrum: m/e=460 (M$^+$ −102), 376 (M$^+$ −186), 358 (M$^+$ −204);

Optical rotation: $[\alpha]_D^{23}$= +8.16° (c=2.55, CHCl$_3$).

REFERENCE EXAMPLE 14

9S-Hydroxy-11R,15S-bis(2-tetrahydropyranyloxy)-16,18-methano-20-methylprost-trans-13-enoic acid 3.58 mg. (0.653 mmol) of 9S-hydroxy-11R,15S-bis(2-tetrahydropyranyloxy)-16,18-methano-20-methylprosta-cis-5,trans-13-dienoic acid (prepared as described in Reference Example 12) in 6 ml. of methanol were subjected to catalytic hydrogenation in the presence of 100 mg. of 5% (w/w) palladium on carbon. Hydrogenation was carried out at room temperature and under atmospheric pressure until 1.2 equivalents of molecular hydrogen were taken up and the starting material could not be detected by thin layer chromatography on a silica gel plate pretreated with silver nitrate [a mixture of chloroform and methanol (20:1) was used as a developing solvent]. After the reaction, the catalyst was filtered off and the resulting filtrate was evaporated to dryness under reduced pressure to yield the title compound (350 mg.) having the following physical characteristics:

NMR (CDCl$_3$): δ; 5.65-5.20 (2H, multiplet), 4.95-4.50 (4H, multiplet), 4.23-3.75 (7H, multiplet), 0.98-0.75 ppm (3H, multiplet);

IR (CHCl$_3$): ν; 3600-2400, 1710, 1130, 1120, 1080, 1020, 1000, 980, 905, 870, 810 cm$^{-1}$;

Mass spectrum: m/e=465 (M$^+$ −85), 464 (M$^+$ −86), 449 (M$^+$ −101), 448 (M$^+$ −102).

REFERENCE EXAMPLE 15

Methyl 9S-hydroxy-11R,15S-bis(2-tetrahydropyranyloxy)-16,18-methano-20-methylprost-trans-13-enoate A solution of 9S-hydroxy-11R,15S-bis(2-tetrahydropyranyloxy)-16,18-methano-20-methylprost-trans-13-enoic acid (293 mg., prepared as described in Reference Example 14) in methanol (6 ml.) was treated with excess diazomethane in diethyl ether. After stirring for a few minutes the reaction mixture was concentrated. The residue was purified by column chromatography on silica gel (5 g.) using a mixture of chloroform and ethanol (6:1) as eluant to give 265 mg. of the pure title compound having the following physical characteristics:

NMR (CDCl$_3$): δ; 5.60-5.06 (2H, multiplet), 4.80-4.50 (2H, multiplet), 4.20-3.26 (7H, multiplet), 3.66 (3H, singlet), 0.98-0.75 ppm (3H, multiplet);

IR (CHCl$_3$): ν; 3500, 1730, 1130, 1110, 1070, 1020, 900, 865 cm$^{-1}$;

Mass spectrum: m/e=464 (M$^+$ −100); 378 (M$^+$ −186), 360 (M$^+$ −204).

REFERENCE EXAMPLE 16

Methyl 9S-hydroxy-11R,15R-bis(2-tetrahydropyranyloxy)-16,16-propanoprosta-cis-5,-trans-13-dienoate A solution of 9S-hydroxy-11R,15R-bis(2-tetrahydropyranyloxy)-16,16-propanoprosta-cis-5,trans-13-dienoic acid (2.92 g.), prepared as described in Example 1 of our British Patent Application No. 10560/75, West German Patent Application P 25 10 818.3 and United States Application Ser. No. 557,437 in methanol (12 ml) was treated with excess diazomethane in diethyl ether. After stirring for a few minutes, the reaction mixture was concentrated. The residue was purified by column chromatography on silica gel (90 g.) [using a mixture of benzene and ethyl acetate (8:1) as eluant] to give 2.18 g. (yield 73%) of the pure title compound having the following physical characteristics:

NMR (CDCl$_3$): δ; 5.60–5.20 (4H, m), 4.80–4.60 (2H, m), 3.64 (3H, s), 0.90 (ppm (3H, t);

IR (CHCl$_3$): ν; 3500, 1730, 1130, 1110, 1075, 1020, 975 cm$^{-1}$;

Mass spectrum: m/e = 474 (M$^+$ − 102).

REFERENCE EXAMPLE 17

Methyl 9S-hydroxy-11R,15R-bis(2-tetrahydropyranyloxy)-16,16-propanoprost-trans-13-enoate 836 mg. of methyl 9S-hydroxy-11R,15R-bis(2-tetrahydropyranyloxy)-16,16-propanoprosta-cis-5,trans-13-dienoate (prepared as described in Reference Example 16) in 30 ml. of methanol were subjected to catalytic hydrogenation in the presence of 300 mg. of 5% w/w palladium on carbon. Hydrogenation was carried out at room temperature and atmospheric pressure until the starting material could not be detected by thin layer chromatography on silica gel plate pre-treated with silver nitrate [a mixture of chloroform and methanol (20:2) was used as a developing solvent]. After the reaction the catalyst was filtered off and the resulting filtrate evaporated to dryness under reduced pressure. Yield of the title compound was 725 mg. (yield 89%). The NMR spectrum shows the absence of the signal due to two hydrogens of the cis-double bond near to δ = 5.50 ppm. The title compound has the following physical characteristics:

NMR (CDCl$_3$): δ; 5.70–5.20 (2H, m), 4.80–4.60 (2H, m), 3.55 (3H, s), 0.90 ppm (3H, t);

IR (CHCl$_3$): ν; 3500, 1730, 1135, 1120, 1080, 1020, 980 cm$^{-1}$;

Mass spectrum: m/e = 374 (M$^+$ − 204).

REFERENCE EXAMPLE 18

Methyl 2-phenylseleno-9S-hydroxy-11R,15R-bis(2-tetrahydropyranyloxy)-16,16-propanoprost-trans-13-enoate A solution of 565 mg. (5.60 mmol) of diisopropylamine in 14 ml. of tetrahydrofuran was cooled to −78° C., and to it 3.7 ml. of a 1.5 M solution of n-butyllithium in n-hexane were added dropwise and the mixture stirred for 15 minutes at −78° C. to give lithium diisopropylamide. To the lithium diisopropylamide solution, 1.28 g. (2.22 mmol) of methyl 9S-hydroxy-11R,15R-bis(2-tetrahydropyranyloxy)16,16-propanoprost-trans-13-enoate (prepared as described in Reference Example 17) in 14 ml. of tetrahydrofuran were added dropwise at −78° C. and the mixture stirred for 20 minutes at the same temperature. A solution of 1.03 g. (3.30 mmol) of diphenyldiselenide in 10 ml. of tetrahydrofuran was added dropwise to the reaction mixture at −78° C. and the reaction mixture was stirred for another 30 minutes at room temperature. The reaction mixture was then acidified with dilute hydrochloric acid, extracted with ethyl acetate, and the extract was washed with water, an aqueous solution of sodium bicarbonate and an aqueous solution of sodium chloride, dried over sodium sulphate and concentrated under reduced pressure. The residue was purified by column chromatography on silica gel (20 g.) using a mixture of benzene and ethyl acetate (5:1) as eluant to give 1.53 g. (yield 94%) of the title compound having the following physical characteristics:

NMR (CDCl$_3$): δ; 7.70–7.20 (5H, m), 5.60–5.30 (2H, m), 4.80–4.60 (2H, m), 3.66 (3H, s), 0.90 ppm (3H, t);

IR (CHCl$_3$): ν; 3500, 1730, 1130, 1080, 1020, 980 cm$^{-1}$;

Mass spectrum: m/e = 530 (M$^+$ − 204).

REFERENCE EXAMPLE 19

Methyl 2-phenylseleno-9S-hydroxy-11R,15S-bis(2-tetrahydropyranyloxy)-16,18-methano-20-methylprost-trans-13-enoate Proceeding as described in Reference Example 18, but using 370 mg. of methyl 9S-hydroxy-11R,15S-bis(2-tetrahydropyranyloxy)-16,18-methano-20-methylprost-trans-13-enoate (prepared as described in Reference Example 15), there were obtained 383 mg. of the title compound having the following physical characteristics:

NMR (CDCl$_3$): δ; 7.80–7.20 (5H, m), 5.70–5.20 (2H, m), 4.80–4.60 (2H, m), 3.65 (3H, s).

EXAMPLE 1

Methyl 9S-hydroxy-11R,15R-bis(2-tetrahydropyranyloxy)-16,16-propanoprosta-trans-2,trans-13-dienoate 1.53 g. of methyl 2-phenylseleno-9S-hydroxy-11R,15R-bis(2-tetrahydropyranyloxy)-16,16-propanoprost-trans-13-enoate (prepared as described in Reference Example 18) were dissolved in 30 ml. of a mixture of ethyl acetate and tetrahydrofuran (1:1) and stirred with 1.2 ml. of 30% hydrogen peroxide at 30° C. for 40 minutes. The reaction mixture was then poured into water, and the organic phase washed with an aqueous solution of sodium carbonate, water and an aqueous solution of sodium chloride, dried over magnesium sulphate and concentrated under reduced pressure to give 1.12 g. (yield 93%) of the title compound having the following physical characteristics:

NMR (CDCl$_3$): δ; 7.12–6.80 (1H, m), 5.93–5.70 (1H, m), 5.60–5.30 (2H, m), 4.80–4.60 (2H, m), 3.72 (3H, s), 0.90 ppm (3H, t);

IR (CHCl$_3$): ν; 3500, 1715, 1655, 1130, 1110, 1070, 1020, 975 cm$^{-1}$;

Mass spectrum: m/e = 372 (M$^+$ − 204).

EXAMPLE 2

Methyl 9S-hydroxy-11R,15S-bis(2-tetrahydropyranyloxy)-16,18-methano-20-methylprosta-trans-2,trans-13-dienoate Proceeding as described in Example 1, but using 383 mg. of methyl 2-phenylseleno-9S-hydroxy-11R,15S-bis(2-tetrahydropyranyloxy)-16,18-methano-20-methyl-prost-trans-13-enoate (prepared as described in Reference Example 19), there were obtained 328 mg. of the title compound having the following physical characteristics:

NMR (CDCl$_3$): δ; 7.15–6.80 (1H, m), 5.91–5.68 (1H, m), 5.60–4.87 (2H, m), 4.78–4.58 (2H, m), 3.70 (3H, s);
Mass spectrum: m/e = 460 (M$^+$ −102).

EXAMPLE 3

9S-Hydroxy-11R,15R-bis(2-tetrahydropyranyloxy)-16,16-propanoprosta-trans-2,trans-13-dienoic acid A solution of methyl 9S-hydroxy-11R,15R-bis(2-tetrahydropyranyloxy)-16,16-propanoprosta-trans-2,trans-13-dienoate (439 mg.), prepared as described in Example 1, in ethanol (13.5 ml.) was treated with 5% (w/v) aqueous potassium hydroxide at 40° C. for 2.5 hours. The reaction mixture was then acidified with aqueous oxalic acid and extracted with methylene chloride. The extract was dried over sodium sulphate and concentrated to yield 394 mg. (yield 92%) of the title compound having the following physical characteristics:

NMR (CDCl$_3$): δ; 7.25–6.90 (1H, m), 6.50–6.10 (2H, D$_2$O exchd), 5.95–5.74 (1H, m), 5.65–5.30 (2H, m), 4.90–4.70 (2H, m), 0.98 ppm (3H, t);
IR (CHCl$_3$): ν; 3700–2300, 3450, 1700, 1650, 1120, 1075, 1020, 980 cm$^{-1}$;
Mass spectrum: m/e = 358 (M$^+$ −204).

EXAMPLE 4

9S-Hydroxy-11R,15S-bis(2-tetrahydropyranyloxy)-16,18-methano-20-methylprosta-trans-2,trans-13-dienoic acid Proceeding as described in Example 3, but using 310 mg. of methyl 9S-hydroxy-11R,15S-bis(2-tetrahydropyranyloxy)-16,18-methano-20-methylprosta-trans-2,trans-13-dienoate, prepared as described in Example 2, there were obtained 301 mg. (yield 99.8%) of the title compound having the following physical characteristics:

NMR (CDCl$_3$): δ; 7.10–6.80 (1H, m), 5.92–5.70 (1H, m), 5.60–5.35 (2H, m), 4.80–4.60 (2H, m), 0.86 (3H, broad t);
IR (CHCl$_3$): ν; 3450, 1700, 1650, 1230–1190, 1120, 1070, 1020 cm$^{-1}$;
Mass spectrum: m/e = 446 (M$^+$ −102).

EXAMPLE 5

9-Oxo-11R,15R-bis(2-tetrahydropyranyloxy)-16,16-propanoprosta-trans-2,trans-13-dienoic acid A solution of manganese sulphate (5.70 g.) in water (28 ml.) was treated with 1.36 ml. of concentrated sulphuric acid followed by chromium trioxide (1.24 g.) at 0° C. After stirring for 5 minutes at 0° C. the solution of oxidizing agent was ready for use.

To a solution of 9S-hydroxy-11R,15R-bis(2-tetrahydropyranyloxy)-16,16-propanoprosta-trans-2,trans-13-dienoic acid (394 mg.), prepared as described in Example 3, in diethyl ether (14 ml.) was added the previously prepared oxidising agent at 0° C. After stirring for 2.5 hours at 0° C. the two phase reaction mixture was diluted with ethyl acetate. The organic layer was washed with a saturated aqueous solution of sodium chloride, dried over magnesium sulphate and concentrated to yield an oily product. The product was purified by short column chromatography on silica gel (4 g.) using diethyl ether as eluant to give 384 mg. (yield 98%) of title product having the following physical characteristics:

NMR (CDCl$_3$): δ; 9.80–9.00 (1H, D$_2$O exchd), 7.37–6.85 (1H, m), 5.91–5.70 (1H, m), 5.70–5.40 (2H, m), 4.87–4.63 (2H, m), 0.91 ppm (3H, t);
IR (CHCl$_3$): ν; 3600–2400, 1740, 1700, 1650, 1140, 1080, 1040, 1030, 980 cm$^{-1}$;
Mass spectrum: m/e = 392 (M$^+$ −168).

EXAMPLE 6

9-Oxo-11R,15S-bis(2-tetrahydropyranyloxy)-16,18-methano-20-methylprosta-trans-2,trans-13-dienoic acid Proceeding as described in Example 5, but using 301 mg. of 9S-hydroxy-11R,15S-bis(2-tetrahydropyranyloxy)-16,18-methano-20-methylprosta-trans-2,trans-13-dienoic acid, prepared as described in Example 4, there were obtained 240 mg. (yield 80.0%) of the title compound having the following physical characteristic:

Mass spectrum: m/e = 444 (M$^+$ −102).

EXAMPLE 7

Methyl 9-oxo-11R,15R-bis(2-tetrahydropyranyloxy)-16,16-propanoprosta-trans-2,trans-13-dienoate Proceeding as described in Example 5, but using methyl 9S-hydroxy-11R,15R-bis(2-tetrahydropyranyloxy)-16,16-propanoprosta-trans-2,trans-13-dienoate (608 mg.), prepared as described in Example 1, the title compound was obtained as a pale yellow oil (591 mg.: yield 97%) having the following physical characteristics:

NMR (CDCl$_3$): δ; 7.12–6.79 (1H, m), 5.92–5.70 (1H, m), 5.70–5.45 (2H, m), 4.85–4.60 (2H, m), 3.72 (3H, s), 0.91 ppm (3H, t);
IR (CHCl$_3$): ν; 1740, 1720, 1660, 1130, 1080, 1035, 975 cm$^{-1}$;
Mass spectrum: m/e = 370 (M$^+$ −204).

EXAMPLE 8

Methyl 9-oxo-11R,15S-bis(2-tetrahydropyranyloxy)-16,18-methano-20-methylprosta-trans-2,trans-13-dienoate Proceeding as described in Example 5, but using 290 mg. of methyl 9S-hydroxy-11R,15S-bis(2-tetrahydropyranyloxy)-16,18-methano-20-methylprosta-trans-2,trans-13-dienoate, prepared as described in Example 2, there were obtained 271 mg. (yield 93.8%) of the title compound having the following physical characteristics:

NMR (CDCl$_3$): δ; 7.10–6.78 (1H, m), 5.91–5.68 (1H, m), 5.68–5.30 (2H, m), 4.80–4.60 (2H, m), 3.73 (3H, s);
Mass spectrum: m/e = 458 (M$^+$ −102).

EXAMPLE 9

16,16-Propano-trans-2,3-didehydro-PGE$_1$

A mixture of 9-oxo-11R,15R-bis(2-tetrahydropyranyloxy)-16,16-propanoprosta-trans-2,trans-13- dienoic acid (384 mg.) prepared as described in Example 5, 21 ml. of aqueous acetic acid (65% v/v) and tetrahydrofuran (2.1 ml.) was stirred at 37° C. for 2.5 hours. The mixture was concentrated using a rotary evaporator to give an oil containing acetic acid which was removed azeotropically with toluene under reduced pressure. The residue was purified by column chromatography on silica gel (12 g.) using a mixture of chloroform and methanol (20:1) as eluant to give 178 mg. (yield 66%) of pure title compound having the following physical characteristics:

NMR (CDCl$_3$): δ; 7.18-6.80 (1H, m), 6.00-5.40 (3H, D$_2$O exchd), 5.90-5.50 (3H, m), 4.23-3.90 (2H, m), 0.92 ppm (3H, t);

IR (CHCl$_3$): ν; 3600-2300, 3400, 1740, 1695, 1650, 980 cm$^{-1}$;

Mass spectrum: m/e = 374 (M$^+$ − 18);

Optical rotation: $[α]_D^{21}$ − 59.1° (c = 1.89, CHCl$_3$);

TLC (developing solvent benzene-tetrahydrofuran-formic acid = 15:5:2); Rf = 0.43.

EXAMPLE 10

16,18-Methano-20-methyl-trans-2,3-didehydro-PGE$_1$

Proceeding as described in Example 9, but using 240 mg. of 9-oxo-11R,15S-bis(2-tetrahydropyranyloxy)-16,18-methano-20-methylprosta-trans-2,trans-13-dienoic acid, prepared as described in Example 6, there were obtained 140 mg. (yield 84%) of pure 16,18-methano-20-methyl-trans-2,3-didehydro-PGE$_1$ having the following physical characteristics:

TLC (developing solvent, benzene:tetrahydrofuran:formic acid = 15:5:2); Rf = 0.38;

NMR (CDCl$_3$): δ; 7.10-6.75 (1H, m), 5.92-5.65 (1H, m), 5.62-5.45 (2H, m), 0.86 (3H, broad t);

IR (CHCl$_3$): ν; 3500, 1745, 1710, 1655, 980 cm$^{-1}$;

Mass spectrum: m/e = 360 (M$^+$ − 18).

EXAMPLE 11

16,16-Propano-trans-2,3-didehydro-PGE$_1$ methyl ester

Proceeding as described in Example 9, but using 553 mg. of methyl 9-oxo-11R,15R-bis(2-tetrahydropyranyloxy)-16,16-propanoprosta-trans-2,trans-13-dienoate, prepared as described in Example 7, there were obtained 352 mg. (yield 90%) of pure 16,16-propano-trans-2,3-didehydro-PGE$_1$ methyl ester having the following physical characteristics:

NMR (CDCl$_3$): δ; 7.10-6.78 (1H, m), 5.90-5.69 (1H, m), 5.70-5.58 (2H, m), 4.15-3.90 (2H, m), 3.72 (3H, s), 3.70-3.50 (2H, D$_2$O exchd), 0.92 ppm (3H, t);

IR (CHCl$_3$): ν; 3400, 1740, 1715, 1655, 975 cm$^{-1}$;

Mass spectrum: m/e = 388 (M$^+$ − 18);

Optical rotation: $[α]_D^{20}$ − 51.1° (c = 2.73, CHCl$_3$);

TLC (developing solvent ethyl acetate-cyclohexane-tetrahydrofuran = 3:6:1): Rf = 0.15.

EXAMPLE 12

16,18-Methano-20-methyl-trans-2,3-didehydro-PGE$_1$ methyl ester

Proceeding as described in Example 9, but using 265 mg. of methyl 9-oxo-11R,15S-bis(2-tetrahydropyranyloxy)-16,18-methano-20-methylprosta-trans-2,trans-13-dienoate prepared as described in Example 8, there were obtained 166 mg. (yield 89.7%) of pure 16,18-methano-20-methyl-trans-2,3-didehydro-PGE$_1$ methyl ester having the following physical characteristics:

TLC (developing solvent, benzene:tetrahydrofuran:formic acid;15:5:2); Rf = 0.48;

NMR (CDCl$_3$): δ; 7.10-6.78 (1H, m), 5.95-5.67 (1H, m), 5.65-5.34 (2H, m), 4.20-3.80 (2H, m), 3.73 (3H, s), 3.55-3.35 (2H, m);

IR (CHCl$_3$): ν; 3400, 1740, 1720, 1650, 1230-1200, 980 cm$^{-1}$.

The present invention includes within its scope pharmaceutical compositions which comprise at least one prostaglandin analogue of general formula VII or a cyclodextrin clathrate thereof or, when R represents a hydrogen atom, a non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or nonaqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses of 16,18-methano-20-methyl-trans-2,3-didehydro-PGE$_1$ per person are generally between 50 μg and 1000 μg by oral administration, and generally between 0.1 μg and 10 μg by intravenous administration in the treatment of *angina pectoris*, and between 100 μg and 1000 μg by oral administration, and between 0.25 μg and 0.50 μg by intravenous administration, in the prevention and treatment of cerebral thrombosis and myocardial infarction. The doses of 16,16-propano-trans-2,3-didehydro-PGE$_1$ are generally between 1.0 and 1000 μg by oral, intravaginal, intrauterine, intravenous, intramuscular and extra-ovular administration in the termination of pregnancy and induction of labour in pregnant female mammals and in the control of conception and menstrual regulation in female mammals. Other prostaglandin analogues of the invention may be used at similar dosage rates to secure the same desired therapeutic effects.

The following Examples illustrate pharmaceutical compositions according to the invention.

EXAMPLE 13

16,18-Methano-20-methyl-trans-2,3-didehydro-PGE$_1$ (5.0 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica, 200 mg.) was added and the powder obtained was machine-filled into one hundred No. 2 hard gelatin capsules to give capsules each containing 50 μg of 16,18-methano-20-methyl-trans-2,3-didehydro-PGE$_1$ which after swallowing of the capsule is released into the stomach.

EXAMPLE 14

16,18-Methano-20-methyl-trans-2,3-didehydro-PGE$_1$ (500 μg.) was dissolved in ethanol (1 ml.) and the solution obtained was added to an aqueous solution (12 ml.) containing sodium carbonate (50 mg.). Aqueous sodium chloride solution (0.9% w/v, 2 ml.) was then added to give a final volume of 15 ml. The solution was then sterilized by passage through a bacteria-retaining filter and placed in 1.5 ml. portions in 5 ml. ampoules, to give 50 μg of 16,18-methano-20-methyl-trans-2,3-didehydro-PGE$_1$ (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

EXAMPLE 15

16,16-Propano-trans-2,3-didehydro-PGE$_1$ (2 mg.) was dissolved in ethanol (10 ml.) mixed with mannitol (18.5 g.), sieved through a 30-mesh sieve, dried at 30° C. for 90 minutes and again sieved through a 30-mesh sieve. Aerosil (microfine silica, 200 mg.) was added and the powder obtained was machine-filled into one hundred No. 2 hard gelatin capsules to give capsules each containing 20 μg of 16,16-propano-trans-2,3-didehydro-PGE$_1$, which after swallowing of the capsule is released into the stomach.

What we claim is:

1. Prostaglandin analogues of the general formula:

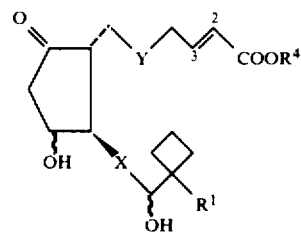

wherein X represents trans-vinylene or ethylene, Y represents cis-vinylene or ethylene, R$^1$ represents a straight- or branched-chain alkyl group containing from 1 to 12 carbon atoms and R$^4$ represents a hydrogen atom or a straight- or branched-chain alkyl group containing from 1 to 12 carbon atoms and the double bond between C$_2$–C$_3$ is trans; and cyclodextrin clathrates of such prostaglandin analogues and, when R$^4$ represents a hydrogen atom, the non-toxic salts thereof.

2. Prostaglandin analogues according to claim 1 wherein Y represents ethylene.

3. Prostaglandin analogues according to claim 1 wherein X represents trans-vinylene.

4. Prostaglandin analogues according to claim 1 wherein R$^4$ represents hydrogen or methyl.

5. Prostaglandin analogues according to claim 1 wherein R$^1$ represents n-propyl or n-butyl.

6. Prostaglandin analogues according to claim 1 wherein the hydroxy groups at the 11 and 15 positions are in the α-configuration.

7. 16,16-Propano-trans-2,3-didehydro-PGE$_1$.

8. 16,16-Propano-trans-2,3-didehydro-PGE$_1$ methyl ester.

9. A pharmaceutical composition useful in the treatment of hypertension, in the treatment of *angina pectoris*, in the prevention and treatment of cerebral thrombosis and myocardial infarction, in the termination of pregnancy and induction of labor in pregnant female mammals and in the control of conception and menstrual regulation in female mammals which comprises, as active ingredient, an effective amount of a prostaglandin analogue as claimed in claim 39 or a cyclodextrin clathrate thereof, and when R$^4$ represents a hydrogen atom, a non-toxic salt thereof, in association with a pharmaceutical carrier or coating.

* * * * *